US010980876B2

(12) United States Patent
Nakagami et al.

(10) Patent No.: US 10,980,876 B2

(45) Date of Patent: Apr. 20, 2021

(54) CONJUGATE VACCINE TARGETING A DISEASE-CAUSING BIOLOGICAL PROTEIN

(71) Applicants: OSAKA UNIVERSITY, Suita (JP); FUNPEP CO., LTD., Ibaraki (JP)

(72) Inventors: Hironori Nakagami, Suita (JP); Ryuichi Morishita, Suita (JP); Akiko Tenma, Ibaraki (JP)

(73) Assignees: OSAKA UNIVERSITY, Suita (JP); FUNPEP CO., LTD., Ibaraki (JP)

( * ) Notice: Subject to any disclaimer, the term of this patent is extended or adjusted under 35 U.S.C. 154(b) by 105 days.

(21) Appl. No.: 16/087,799

(22) PCT Filed: Mar. 24, 2017

(86) PCT No.: PCT/JP2017/012187

§ 371 (c)(1),
(2) Date: Sep. 24, 2018

(87) PCT Pub. No.: WO2017/164409

PCT Pub. Date: Sep. 28, 2017

(65) Prior Publication Data

US 2019/0105388 A1 Apr. 11, 2019

(30) Foreign Application Priority Data

Mar. 25, 2016 (JP) ............................ JP2016-062872

(51) Int. Cl.

*A61K 39/395* (2006.01)
*A61K 39/39* (2006.01)
*A61K 39/00* (2006.01)
*A61P 37/04* (2006.01)

(52) U.S. Cl.

CPC .............. *A61K 39/39* (2013.01); *A61K 39/00* (2013.01); *A61K 39/00114* (2018.08); *A61K 39/39533* (2013.01); *A61P 37/04* (2018.01); *A61K 2039/55527* (2013.01)

(58) Field of Classification Search

None
See application file for complete search history.

(56) References Cited

U.S. PATENT DOCUMENTS

| | | | | |
|---|---|---|---|---|
| 10,112,978 | B2 * | 10/2018 | Nakagami .............. | A61K 38/00 |
| 2007/0055049 | A1 | 3/2007 | Grey et al. | |
| 2012/0172287 | A1 * | 7/2012 | Gemba .................. | A61P 17/02 514/2.4 |
| 2013/0064788 | A1 * | 3/2013 | Barnes .................... | A61P 37/02 424/85.2 |
| 2016/0101032 | A1 | 4/2016 | Nakagami et al. | |
| 2016/0193308 | A1 | 7/2016 | Nakagami et al. | |
| 2016/0319013 | A1 | 11/2016 | Koriyama et al. | |
| 2017/0275336 | A1 | 9/2017 | Nakagami et al. | |

FOREIGN PATENT DOCUMENTS

| | | | |
|---|---|---|---|
| WO | WO 2010/089940 | A1 | 8/2010 |
| WO | WO 2014/157485 | A1 | 10/2014 |
| WO | WO 2015/033831 | A1 | 3/2015 |
| WO | WO 2015/099167 | A1 | 7/2015 |
| WO | WO 2016/047763 | A1 | 3/2016 |

OTHER PUBLICATIONS

European Patent Office, Extended European Search Report in European Patent Application No. 17770449.1 (dated Oct. 8, 2019).
Lauwerys et al., “Down-Regulation of Interferon Signature in Systemic Lupus Erythematosus Patients by Active Immunization With Interferon α-Kinoid,” *Arthritis Rheum.*, 65(2): 447-456 (2013).
Van Houten et al., “Filamentous phage as an immunogenic carrier to elicit focused antibody responses against a synthetic peptide,” *Vaccine*, 24(19): 4188-4200 (2006).
Japanese Patent Office, International Search Report in International Patent Application No. PCT/JP2017/012187 (dated May 16, 2017).
Tenma et al., “AJP001, a novel helper T-cell epitope, induces a humoral immune response with activation of innate immunity when included in a peptide vaccine,” *FASEB BioAdvances*, 1(12): 760-772 and Supplemental Information (2019).
Nakamaru et al., “A novel angiotensin II peptide vaccine without an adjuvant inmice,” *J. Hypertens.*, 38: doi: 10.1097/HJH.0000000000002597 (2020).

* cited by examiner

*Primary Examiner* — Yunsoo Kim
(74) *Attorney, Agent, or Firm* — Leydig, Voit & Mayer, Ltd.

(57) ABSTRACT

The present invention provides a vaccine containing a complex of a peptide consisting of the amino acid sequence of SEQ ID NO: 1 and an epitope of a disease-causing biological protein such as DPP4, IL-17A, IgE, S100A9 or PCSK9, which vaccine uses a less antigenic carrier protein and is capable of inducing antibody production to serve as an effective vaccine.

10 Claims, 18 Drawing Sheets

Specification includes a Sequence Listing.

Fig. 9

(A) OSK1-IL-21 Amino acid analysis

Product: L17001-A

Structure:

Ac-ELKLI FLHRL KRLRK RLKRK XRPSD YLNR-$NH_2$

X= ε -Acp

Synthesis Code No.: AG-316

Lot No.: 751-605191

Appearance: White freeze-dried powder

Amino acid analysis values:

Hydrolysis conditions: 6N HCl, 110℃, 22hrs.

Asp(2)2.01, Ser(1)0.89, Glu(1)1.00, Ile(1)0.98,
Leu(7)7.02, Tyr(1)0.97, Phe(1)0.98, Lys(5)4.97,
$NH_3$(2)2.09, His(1)1.00, Arg(7)6.95, Pro(1)0.99,
ε -Acp(1)1.11

Purity (HPLC): 95.8 % (Criteria of acceptance: 90% or higher)

ESI-MS: MW = 3801.4 (Theor. 3801.6 )

(B) OSK1-IL-21 HPLC analysis

Sample name: AG-316 Sample ID: Lot.751-605191 Data File: LC201-01.lcd

Sample: AG - 316 Lot. 751-605191
Column: Zorbax 300SB-C18 (4.6mmI.D.x 150mm)
Eluent: 15-65% $CH_3CN$/0.1% TFA (25min)
Temp.: 50 °C Flow rate: 1.0 ml/min.
Detector: 220 nm
Load: 10 µl (conc. 0.34 mg/ 340 µl 0.1% TFAaq.)

<PDA Chromatogram>

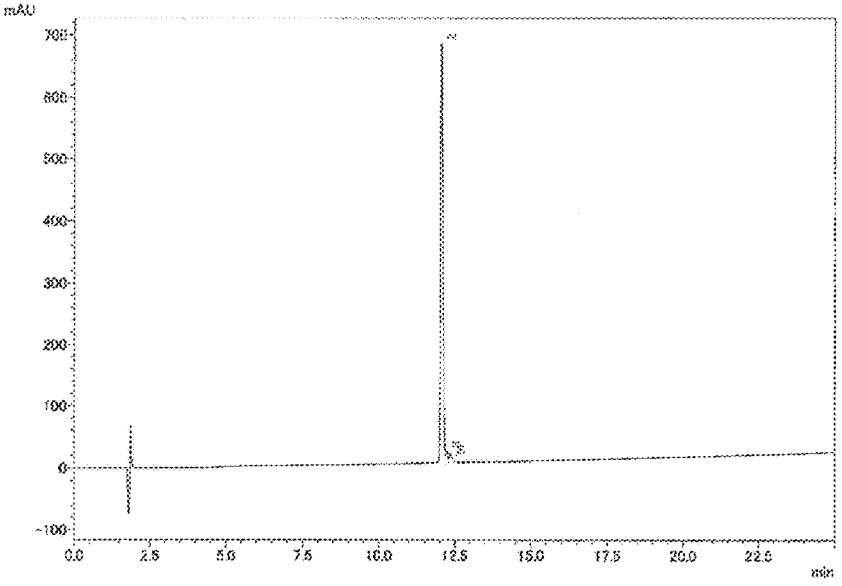

Fig. 10

(A) OSK1-IL-31 Amino acid analysis

Product: L17007-A

Structure:

Ac-ELKLI FLHRL KRLRK RLKRK XNRST SPW-$NH_2$

X= ε -Acp

Synthesis Code No.: AG-471

Lot No.: 751-610112

Appearance: White freeze-dried powder

Amino acid analysis values:

Hydrolysis conditions: 4N Methanesulfonic Acid (with 0.2% 3-(2-Aminoethyl) indole), 150℃. 2.5hrs.

Asp(1)1.01, Thr(1)0.87, Ser(2)1.49, Glu(1)0.99,
Ile(1)0.99, Leu(6)6.00, Phe(1)0.99, Lys(5)5.01,
$NH_3$(2)2.74, His(1)1.00, Arg(6)6.01, Pro(1)1.01,
Trp(1)+ ε -Acp(1)1.92

Purity (HPLC): 99.2 % (Criteria of acceptance: 90% or higher)

ESI-MS: MW = 3628.2 (Theor. 3628.4 )

(B) OSK1-IL-31 HPLC analysis

Sample name: AG-471 Sample ID: Lot.751-610112 Data File: LC121-04.lcd

Sample: AG-471 Lot. 751-610112
Column: Zorbax 300SB-C18 (4.6mmI.D.x 150mm)
Eluent: 15-85% CH3CN/0.1% TFA (25min)
Temp.: 30 ℃ Flow rate: 1.0 ml/min.
Detector: 220 nm
Load: 3 ul (conc. 0.30 mg/300 μl 0.1% TFA)

PDA Chromatogram

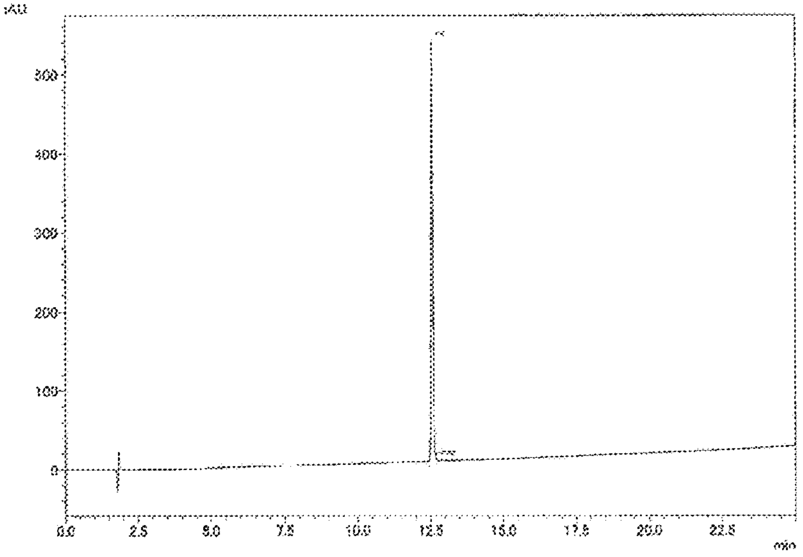

Fig. 11

(A) OSK1-IL-32 Amino acid analysis

Product: L17008-A

Structure:

Ac-ELKLI FLHRL KRLRK RLKRK XLHRN EDF-$NH_2$

X= ε -Acp

Synthesis Code No.: AG-473

Lot No.: 751-610041

Appearance: White freeze-dried powder

Amino acid analysis values:

Hydrolysis conditions: 6N HCl, 110℃, 22hrs.

Asp(2)2.01, Glu(2)2.00, Ile(1)0.97, Leu(7)6.91,
Phe(1)0.97, Lys(5)4.96, $NH_3$(2)2.05, His(2)1.98,
Arg(6)5.96, Pro(1)1.00, ε -Acp(1)1.09

Purity (HPLC): 97.6 % (Criteria of acceptance: 90% or higher)

ESI-MS: MW = 3661.5 (Theor. 3661.5 )

(B) OSK1-IL-32 HPLC analysis

Sample name: AG-473 Sample ID: Lot.751-610041 Date File: LC051-03.lcd

Sample: AG-473 Lot. 751-610041
Column: Zorbax 300SB-C18 (4.6mm I.D.x 150mm)
Eluent: 15-65% CH3CN/0.1% TFA (25min)
Temp.: 50 °C Flow rate: 1.0 ml/min.
Detector: 220 nm
Load: 10 ul (conc. 0.77 mg/330 µl 0.1%TFA)

<PDA Chormatogram>

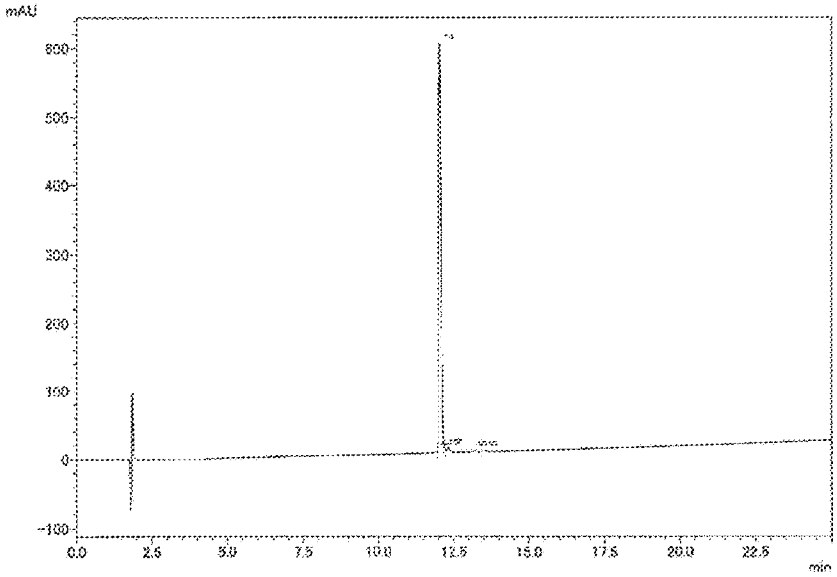

Fig. 12

(A) OSK1-IL-40 Amino acid analysis

Product: LJ7011-A

Structure:

Ac-ELKLI FLHRL KRLRK RLKRK XVSSR RPSDY LNR-$NH_2$

X= ε -Acp

Synthesis Code No. : AG-479

Lot No. : 751-610122

Appearance: White freeze-dried powder

Amino acid analysis values:

Hydrolysis conditions: 6N HCl, 110℃, 22hrs.

Asp(2)2.01, Ser(3)2.70, Glu(1)1.00, Val(1)1.00,
Ile(1)1.00, Leu(7)7.00, Tyr(1)1.00, Phe(1)0.99,
Lys(5)4.99, $NH_3$(2)2.39, His(1)1.00, Arg(8)8.00,
Pro(1)1.00, ε -Acp(1)1.12

Purity (HPLC) : 97.8 % (Criteria of acceptance: 90% or higher )

ESI-MS : MW = 4230.9 ( Theor. 4231.1 )

(B) OSK1-IL-40 HPLC analysis

Sample name : AG-479 Sample ID : Lot.751-610122 Data File : LC131-03.lcd

Sample : AG-479 Lot. 751-610122
Column : Zorbax 300SB-C18 (4.6mmI.D.x 150mm)
Eluent : 15-65% CH3CN/0.1% TFA (25min)
Temp. : 50 ℃ Flow rate : 1.0 ml/min.
Detector : 220 nm
Load : 10 μl (conc. 0.30 mg/300 μl 0.1% TFA )

<PDA Chromatogram>

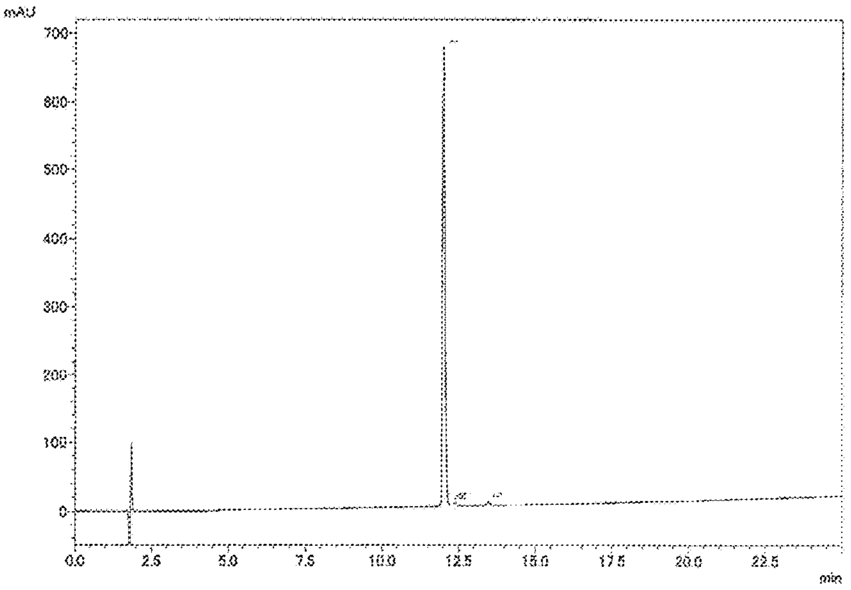

SEQUENCE LISTING

```
<160> NUMBER OF SEQ ID NOS: 41

<210> SEQ ID NO 1
<211> LENGTH: 20
<212> TYPE: PRT
<213> ORGANISM: Artificial Sequence
<220> FEATURE:
<223> OTHER INFORMATION: synthesized peptide

<400> SEQUENCE: 1

Glu Leu Lys Leu Ile Phe Leu His Arg Leu Lys Arg Leu Arg Lys Arg
1               5                   10                  15

Leu Lys Arg Lys
            20


<210> SEQ ID NO 2
<211> LENGTH: 9
<212> TYPE: PRT
<213> ORGANISM: Homo sapiens

<400> SEQUENCE: 2

Glu Asn Ser Thr Phe Asp Glu Phe Gly
1               5


<210> SEQ ID NO 3
<211> LENGTH: 9
<212> TYPE: PRT
<213> ORGANISM: Homo sapiens

<400> SEQUENCE: 3
```

Asn Lys Arg Gln Leu Ile Thr Glu Glu
1 5

<210> SEQ ID NO 4
<211> LENGTH: 10
<212> TYPE: PRT
<213> ORGANISM: Homo sapiens

<400> SEQUENCE: 4

Lys Asn Thr Tyr Arg Leu Lys Leu Tyr Ser
1 5 10

<210> SEQ ID NO 5
<211> LENGTH: 10
<212> TYPE: PRT
<213> ORGANISM: Homo sapiens

<400> SEQUENCE: 5

Tyr Ser Asp Glu Ser Leu Gln Tyr Pro Lys
1 5 10

<210> SEQ ID NO 6
<211> LENGTH: 10
<212> TYPE: PRT
<213> ORGANISM: Homo sapiens

<400> SEQUENCE: 6

Pro Pro His Phe Asp Lys Ser Lys Lys Tyr
1 5 10

<210> SEQ ID NO 7
<211> LENGTH: 10
<212> TYPE: PRT
<213> ORGANISM: Homo sapiens

<400> SEQUENCE: 7

Gly Leu Pro Thr Pro Glu Asp Asn Leu Asp
1 5 10

<210> SEQ ID NO 8
<211> LENGTH: 9
<212> TYPE: PRT
<213> ORGANISM: Homo sapiens

<400> SEQUENCE: 8

Phe Ser Lys Glu Ala Lys Tyr Tyr Gln
1 5

<210> SEQ ID NO 9
<211> LENGTH: 15
<212> TYPE: PRT
<213> ORGANISM: Homo sapiens

<400> SEQUENCE: 9

Asn Ser Ser Val Phe Leu Glu Asn Ser Thr Phe Asp Glu Phe Gly
1 5 10 15

<210> SEQ ID NO 10
<211> LENGTH: 8
<212> TYPE: PRT
<213> ORGANISM: Homo sapiens

<400> SEQUENCE: 10

Arg Ser Ser Asp Tyr Tyr Asn Arg

-continued 1 5

<210> SEQ ID NO 11
<211> LENGTH: 15
<212> TYPE: PRT
<213> ORGANISM: Homo sapiens

<400> SEQUENCE: 11

Pro Lys Arg Ser Ser Asp Tyr Tyr Asn Arg Ser Thr Ser Pro Trp
1 5 10 15

<210> SEQ ID NO 12
<211> LENGTH: 11
<212> TYPE: PRT
<213> ORGANISM: Homo sapiens

<400> SEQUENCE: 12

Tyr Gln Cys Arg Val Thr His Pro His Leu Pro
1 5 10

<210> SEQ ID NO 13
<211> LENGTH: 10
<212> TYPE: PRT
<213> ORGANISM: Homo sapiens

<400> SEQUENCE: 13

Gly His His His Lys Pro Gly Leu Gly Glu
1 5 10

<210> SEQ ID NO 14
<211> LENGTH: 10
<212> TYPE: PRT
<213> ORGANISM: Homo sapiens

<400> SEQUENCE: 14

Leu Arg Pro Arg Gly Gln Pro Asn Gln Cys
1 5 10

<210> SEQ ID NO 15
<211> LENGTH: 9
<212> TYPE: PRT
<213> ORGANISM: Homo sapiens

<400> SEQUENCE: 15

Ser Arg His Leu Ala Gln Ala Ser Gln
1 5

<210> SEQ ID NO 16
<211> LENGTH: 10
<212> TYPE: PRT
<213> ORGANISM: Homo sapiens

<400> SEQUENCE: 16

Ser Arg Ser Gly Lys Arg Arg Gly Glu Arg
1 5 10

<210> SEQ ID NO 17
<211> LENGTH: 9
<212> TYPE: PRT
<213> ORGANISM: Mus musculus

<400> SEQUENCE: 17

Glu Asn Ser Thr Phe Glu Ser Phe Gly
1 5

<210> SEQ ID NO 18
<211> LENGTH: 10
<212> TYPE: PRT
<213> ORGANISM: Mus musculus

<400> SEQUENCE: 18

Lys Ser Thr Phe Arg Val Lys Ser Tyr Ser
1               5                   10

<210> SEQ ID NO 19
<211> LENGTH: 10
<212> TYPE: PRT
<213> ORGANISM: Mus musculus

<400> SEQUENCE: 19

Gly Leu Pro Ile Pro Glu Asp Asn Leu Asp
1               5                   10

<210> SEQ ID NO 20
<211> LENGTH: 15
<212> TYPE: PRT
<213> ORGANISM: Mus musculus

<400> SEQUENCE: 20

Asn Ser Ser Ile Phe Leu Glu Asn Ser Thr Phe Glu Ser Phe Gly
1               5                   10                  15

<210> SEQ ID NO 21
<211> LENGTH: 8
<212> TYPE: PRT
<213> ORGANISM: Mus musculus

<400> SEQUENCE: 21

Arg Pro Ser Asp Tyr Leu Asn Arg
1               5

<210> SEQ ID NO 22
<211> LENGTH: 15
<212> TYPE: PRT
<213> ORGANISM: Mus musculus

<400> SEQUENCE: 22

Ser Arg Arg Pro Ser Asp Tyr Leu Asn Arg Ser Thr Ser Pro Trp
1               5                   10                  15

<210> SEQ ID NO 23
<211> LENGTH: 11
<212> TYPE: PRT
<213> ORGANISM: Mus musculus

<400> SEQUENCE: 23

Tyr Gln Cys Ile Val Asp His Pro Asp Phe Pro
1               5                   10

<210> SEQ ID NO 24
<211> LENGTH: 10
<212> TYPE: PRT
<213> ORGANISM: Mus musculus

<400> SEQUENCE: 24

Gly His Ser His Gly Lys Gly Cys Gly Lys
1               5                   10

<210> SEQ ID NO 25

<211> LENGTH: 10
<212> TYPE: PRT
<213> ORGANISM: Mus musculus

<400> SEQUENCE: 25

Pro Ala Leu Arg Ser Arg Arg Gln Pro Gly
1 5 10

<210> SEQ ID NO 26
<211> LENGTH: 9
<212> TYPE: PRT
<213> ORGANISM: Mus musculus

<400> SEQUENCE: 26

Cys Arg Ser Arg Pro Ser Ala Lys Ala
1 5

<210> SEQ ID NO 27
<211> LENGTH: 10
<212> TYPE: PRT
<213> ORGANISM: Mus musculus

<400> SEQUENCE: 27

Ser Phe Ser Arg Ser Gly Arg Arg Arg Gly
1 5 10

<210> SEQ ID NO 28
<211> LENGTH: 9
<212> TYPE: PRT
<213> ORGANISM: Mus musculus

<400> SEQUENCE: 28

Arg Met Phe Pro Asn Ala Pro Tyr Leu
1 5

<210> SEQ ID NO 29
<211> LENGTH: 11
<212> TYPE: PRT
<213> ORGANISM: Homo sapiens

<400> SEQUENCE: 29

Cys Pro Asn Ser Glu Asp Lys Asn Phe Pro Arg
1 5 10

<210> SEQ ID NO 30
<211> LENGTH: 10
<212> TYPE: PRT
<213> ORGANISM: Homo sapiens

<400> SEQUENCE: 30

Arg Asn Glu Asp Pro Glu Arg Tyr Pro Ser
1 5 10

<210> SEQ ID NO 31
<211> LENGTH: 7
<212> TYPE: PRT
<213> ORGANISM: Homo sapiens

<400> SEQUENCE: 31

Asn Arg Ser Thr Ser Pro Trp
1 5

<210> SEQ ID NO 32
<211> LENGTH: 7
<212> TYPE: PRT

-continued

<213> ORGANISM: Homo sapiens

<400> SEQUENCE: 32

Leu His Arg Asn Glu Asp Pro
1 5

<210> SEQ ID NO 33
<211> LENGTH: 9
<212> TYPE: PRT
<213> ORGANISM: Homo sapiens

<400> SEQUENCE: 33

Arg Tyr Pro Ser Val Ile Trp Glu Ala
1 5

<210> SEQ ID NO 34
<211> LENGTH: 10
<212> TYPE: PRT
<213> ORGANISM: Homo sapiens

<400> SEQUENCE: 34

Pro Lys Arg Ser Ser Asp Tyr Tyr Asn Arg
1 5 10

<210> SEQ ID NO 35
<211> LENGTH: 12
<212> TYPE: PRT
<213> ORGANISM: Homo sapiens

<400> SEQUENCE: 35

Thr Asn Pro Lys Arg Ser Ser Asp Tyr Tyr Asn Arg
1 5 10

<210> SEQ ID NO 36
<211> LENGTH: 14
<212> TYPE: PRT
<213> ORGANISM: Homo sapiens

<400> SEQUENCE: 36

Thr Asn Thr Asn Pro Lys Arg Ser Ser Asp Tyr Tyr Asn Arg
1 5 10

<210> SEQ ID NO 37
<211> LENGTH: 11
<212> TYPE: PRT
<213> ORGANISM: Mus musculus

<400> SEQUENCE: 37

Cys Pro Asn Thr Glu Ala Lys Asp Phe Leu Gln
1 5 10

<210> SEQ ID NO 38
<211> LENGTH: 10
<212> TYPE: PRT
<213> ORGANISM: Mus musculus

<400> SEQUENCE: 38

Arg Asn Glu Asp Pro Asp Arg Tyr Pro Ser
1 5 10

<210> SEQ ID NO 39
<211> LENGTH: 10
<212> TYPE: PRT
<213> ORGANISM: Mus musculus -continued

```
<400> SEQUENCE: 39

Ser Arg Arg Pro Ser Asp Tyr Leu Asn Arg
1               5                   10


<210> SEQ ID NO 40
<211> LENGTH: 12
<212> TYPE: PRT
<213> ORGANISM: Mus musculus

<400> SEQUENCE: 40

Val Ser Ser Arg Arg Pro Ser Asp Tyr Leu Asn Arg
1               5                   10


<210> SEQ ID NO 41
<211> LENGTH: 14
<212> TYPE: PRT
<213> ORGANISM: Mus musculus

<400> SEQUENCE: 41

Ala Lys Val Ser Ser Arg Arg Pro Ser Asp Tyr Leu Asn Arg
1               5                   10
```

CONJUGATE VACCINE TARGETING A DISEASE-CAUSING BIOLOGICAL PROTEIN

CROSS-REFERENCE TO RELATED APPLICATIONS

This patent application is the U.S. national phase of International Patent Application No. PCT/JP2017/012187, filed Mar. 24, 2017, which claims the benefit of Japanese Patent Application No. 2016-062872, filed on Mar. 25, 2016, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 7,053 bytes ASCII (Text) file named "740423SequenceListing.txt," created Sep. 14, 2017

TECHNICAL FIELD

The present invention relates to a conjugate vaccine targeting a disease-causing biological protein.

BACKGROUND ART

Vaccine techniques have been long used for the prevention of infections such as smallpox, and have recently been attempted to be used for the treatment of cancer, life-style related diseases, etc. Some therapeutic vaccines use a carrier protein conjugated to an epitope of a target protein, which stimulates immune responses, for example, the induction of antibodies against the target protein. Known examples of such a carrier protein include KLH (keyhole limpet hemocyanin), OVA (ovalbumin) and BSA (bovine serum albumin). For example, for the treatment of systemic lupus erythematosus (SLE), the administration of a vaccine composed of a modified form of INF-α as an antigen moiety conjugated to KLH has been attempted (Non Patent Literature 1).

However, KLH, OVA, BSA and other carrier proteins are antigenic in themselves, and this antigenicity can sometimes pose a problem in the case where a moderately antigenic epitope conjugated to such a carrier protein is used for immunization (Non Patent Literature 2).

The present inventors disclose the use of a conjugate of a DPP4 epitope peptide and KLH for the prevention or treatment of diabetes mellitus (Patent Literature 1). In addition, the present inventors disclose the use of a DNA vaccine containing a polynucleotide encoding an IL-17A epitope peptide and a polynucleotide encoding a core antigen polypeptide of hepatitis B virus for the prevention or treatment of diseases in which IL-17A is involved as a precipitating factor (e.g., systemic lupus erythematosus (SLE), articular rheumatism, etc.) (Patent Literature 2).

CITATION LIST

Patent Literature

Patent Literature 1: WO2015/033831
Patent Literature 2: WO2015/099167
Non Patent Literature 1: ARTHRITIS & RHEUMATISM Vol. 65, No. 2, February 2013, pp 447-456.
Non Patent Literature 2: N. E. van Houten, M. B. Zwick, A. Menendez, and J. K. Scott Vaccine. 2006 May 8; 24(19): 4188-4200.

SUMMARY OF INVENTION

Technical Problem

An object of the present invention is to provide a vaccine which contains a complex of a less antigenic carrier protein conjugated to an epitope of a disease-causing biological protein and is capable of inducing antibody production to serve as an effective vaccine.

Solution to Problem

The present invention includes the following to achieve the above-mentioned object.

(1) A vaccine comprising a complex of a peptide consisting of an amino acid sequence that is the same or substantially the same as the amino acid sequence of SEQ ID NO: 1 and an epitope of a disease-causing biological protein.

(2) The vaccine according to the above (1), wherein the biological protein is one kind selected from the group consisting of DPP4, IL-17A, IgE, S100A9 and PCSK9.

(3) The vaccine according to the above (2), wherein the epitope of IL-17A is a peptide consisting of the amino acid sequence of any of SEQ ID NOs: 10, 11 and 29 to 36, or a peptide consisting of an amino acid sequence that is the same as the amino acid sequence of any of SEQ ID NOs: 10, 11 and 29 to 36 except for 1 or 2 amino acid deletions, substitutions or additions.

(4) The vaccine according to the above (2), wherein the epitope of DPP4 is a peptide consisting of the amino acid sequence of any of SEQ ID NOs: 2 to 9, or a peptide consisting of an amino acid sequence that is the same as the amino acid sequence of any of SEQ ID NOs: 2 to 9 except for 1 or 2 amino acid deletions, substitutions or additions.

(5) The vaccine according to the above (2), wherein the epitope of IgE is a peptide consisting of the amino acid sequence of SEQ ID NO: 12, or a peptide consisting of an amino acid sequence that is the same as the amino acid sequence of SEQ ID NO: 12 except for 1 or 2 amino acid deletions, substitutions or additions.

(6) The vaccine according to the above (2), wherein the epitope of S100A9 is a peptide consisting of the amino acid sequence of SEQ ID NO: 13, or a peptide consisting of an amino acid sequence that is the same as the amino acid sequence of SEQ ID NO: 13 except for 1 or 2 amino acid deletions, substitutions or additions.

(7) The vaccine according to the above (2), wherein the epitope of PCSK9 is a peptide consisting of the amino acid sequence of any of SEQ ID NOs: 14 to 16, or a peptide consisting of an amino acid sequence that is the same as the amino acid sequence of any of SEQ ID NOs: 14 to 16 except for 1 or 2 amino acid deletions, substitutions or additions.

(8) The vaccine according to any one of the above (1) to (7), wherein the epitope of the biological protein is conjugated to the peptide consisting of the amino acid sequence of SEQ ID NO: 1 via ε-aminocaproic acid.

(9) The vaccine according to any one of the above (1) to (8), wherein the amino acid at the N-terminus of the complex is acetylated.

(10) The vaccine according to any one of the above (1) to (9), wherein the amino acid at the C-terminus of the complex is amidated.

(11) An immunogenic composition comprising a complex of a peptide consisting of the amino acid sequence of SEQ ID NO: 1 and an epitope of a disease-causing biological protein.

(12) The immunogenic composition according to the above (11), wherein the biological protein is one kind selected from the group consisting of DPP4, IL-17A, IgE, S100A9 and PCSK9.

(13) A method for preventing or treating a disease caused by a biological protein, the method comprising administering, to an animal, an effective amount of a complex of a peptide consisting of an amino acid sequence that is the same or substantially the same as the amino acid sequence of SEQ ID NO: 1 and an epitope of the biological protein.

(14) A complex for use in prevention or treatment of a disease caused by a biological protein, the complex of a peptide consisting of an amino acid sequence that is the same or substantially the same as the amino acid sequence of SEQ ID NO: 1 and an epitope of the biological protein.

(15) Use of a complex of a peptide consisting of an amino acid sequence that is the same or substantially the same as the amino acid sequence of SEQ ID NO: 1 and an epitope of a disease-causing biological protein, for production of a medicament for prevention or treatment of a disease caused by the biological protein.

Advantageous Effects of Invention

The present invention provides a vaccine which contains a complex of a less antigenic carrier protein conjugated to an epitope of a disease-causing biological protein and is capable of inducing antibody production to serve as an effective vaccine.

BRIEF DESCRIPTION OF DRAWINGS

FIG. 9 shows (A) the results of amino acid analysis and (B) the results of HPLC analysis of an OSK-1-DPP4 conjugate composed of the OSK-1 peptide conjugated to a mouse IL-17A epitope peptide (SEQ ID NO: 21) via an ε-Acp linker.

FIG. 10 shows (A) the results of amino acid analysis and (B) the results of HPLC analysis of an OSK-1-DPP4 conjugate composed of the OSK-1 peptide conjugated to a mouse IL-17A epitope peptide (SEQ ID NO: 31) via an ε-Acp linker.

FIG. 11 shows (A) the results of amino acid analysis and (B) the results of HPLC analysis of an OSK-1-DPP4 conjugate composed of the OSK-1 peptide conjugated to a mouse IL-17A epitope peptide (SEQ ID NO: 32) via an ε-Acp linker.

FIG. 12 shows (A) the results of amino acid analysis and (B) the results of HPLC analysis of an OSK-1-DPP4 conjugate composed of the OSK-1 peptide conjugated to a mouse IL-17A epitope peptide (SEQ ID NO: 40) via an ε-Acp linker.

DESCRIPTION OF EMBODIMENTS

Figure 1:
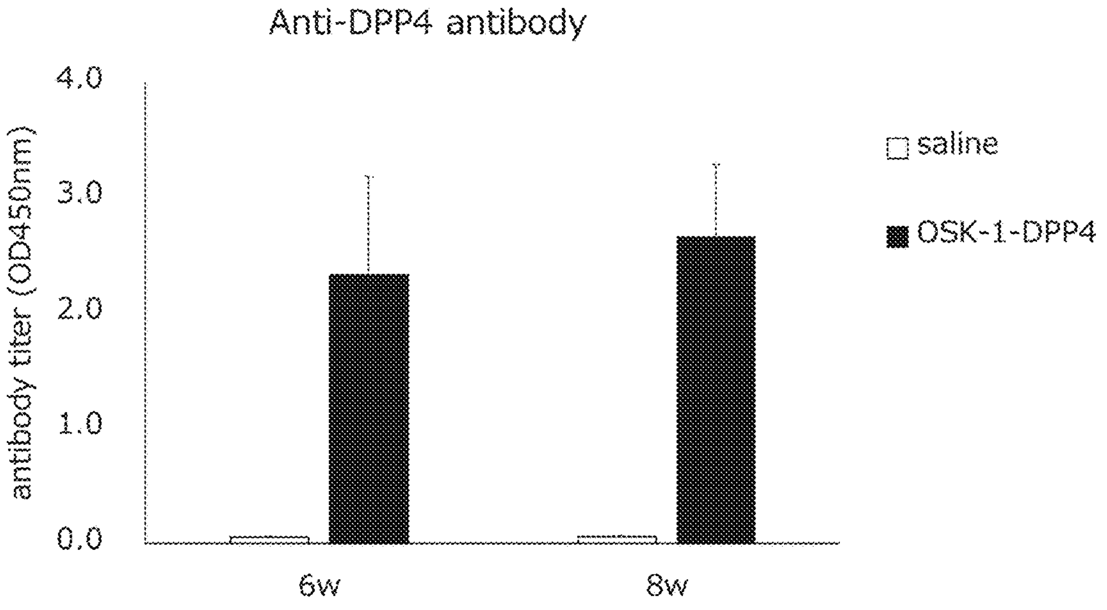
FIG. 1 shows the antibody production-inducing effect of an OSK-1-DPP4 conjugate composed of an OSK-1 peptide (SEQ ID NO: 1) conjugated to a mouse DPP4 epitope peptide (SEQ ID NO: 17) via an ε-Acp linker.

The present invention provides a conjugate vaccine targeting a disease-causing biological protein. The vaccine of the present invention contains a complex of a peptide consisting of an amino acid sequence that is the same or substantially the same as the amino acid sequence of SEQ ID NO: 1 (ELKLIFLHRLKRLRKRLKRK) and an epitope of the disease-causing biological protein. As used herein, the peptide consisting of the amino acid sequence of SEQ ID NO: 1 may be referred to as an OSK-1 peptide or OSK-1. In addition, as used herein, the terms "conjugate" and "complex" are interchangeably used.

As used herein, the term "vaccine" means a composition containing an immunogen which elicits immunoreaction after administered to an animal. Therefore, stated in another way, the vaccine of the present invention is an immunogenic composition. The vaccine of the present invention is not limited to a vaccine to be administered for preventive purposes, and may be a vaccine to be administered for therapeutic purposes after disease onset.

The amino acid sequence that is substantially the same as the amino acid sequence of SEQ ID NO: 1 is, for example, an amino acid sequence that is the same as the amino acid sequence of SEQ ID NO: 1 except for 1 to 4 amino acid deletions, substitutions or additions. Preferred is an amino acid sequence that is the same as the amino acid sequence of SEQ ID NO: 1 except for deletions, substitutions or additions of 1 to 3 amino acids, more preferably 1 or 2 amino acids, still more preferably one amino acid. The peptide consisting of an amino acid sequence that is substantially the same as the amino acid sequence of SEQ ID NO: 1 is preferably a peptide having an activity that is substantially the same as that of the peptide consisting of the amino acid sequence of SEQ ID NO: 1. Specifically, a complex of this peptide and an epitope of a biological protein has an antibody production-inducing capability comparable (for example, about 0.5- to 2-fold) to that of a complex of the peptide consisting of the amino acid sequence of SEQ ID NO: 1 and the same epitope of the biological protein.

The disease-causing biological protein is not particularly limited, and examples include DPP4, IL-17A, IgE, S100A9 and PCSK9. As used herein, the term "biological protein" means an endogenous protein.

DPP4 (dipeptidyl peptidase-4) is an enzyme that degrades incretin, which is involved in insulin secretion. Incretin is a gastrointestinal hormone that promotes insulin secretion during hyperglycemia such as postprandial hyperglycemia to reduce the blood glucose level. Therefore, the inhibition of the function of DPP4 for preventing the degradation of incretin increases incretin concentration, thereby promoting insulin secretion and thus improving the symptoms of diabetes mellitus. Based on this mechanism, many DPP4 inhibitors have been developed and approved as antidiabetic drugs. Therefore, vaccines capable of inducing an anti-DPP4 antibody are expected to treat diabetes mellitus.

The epitope of human DPP4 used for an OSK-1-DPP4 conjugate is not particularly limited as long as it is an epitope capable of inducing the production of an antibody that inhibits the functions of DPP4 (neutralizing antibody). Preferable examples of the epitope include peptides consisting of any of the following amino acid sequences.

ENSTFLEFG (SEQ ID NO: 2)

NKRQLTTFE (SEQ ID NO: 3)

KNTYRLKLYS (SEQ ID NO: 4)

YSDESLOYPK (SEQ ID NO: 5)

PPHFDKEKEY (SEQ ID NO: 6)

GLPTPEDNLD (SEQ ID NO: 7)

FSKEAKYYQ (SEQ ID NO: 8)

NSSVYLENSTFLEFG (SEQ ID NO: 9)

The accession numbers of the amino acid sequence of human DPP4 and the nucleotide sequence of the gene encoding human DPP4 are NP_001926 (NCBI) and NM_001935 (NCBI), respectively.

Peptides which consist of an amino acid sequence that is the same as the amino acid sequence of any of SEQ ID NOs: 2 to 9 except for 1 or 2 amino acid deletions, substitutions or additions and which are capable of inducing the production of an antibody that inhibits the functions of DPP4 are also preferable as the epitope of human DPP4 used for the OSK-1-DPP4 conjugate.

IL-17A (interleukin-17A) is a homodimeric glycoprotein and is also referred to simply as IL-17. IL-17A, which is mainly produced by activated T cells, acts on a wide range of cells such as fibroblasts, epithelial cells, vascular endothelial cells and macrophages to recruit various factors such as inflammatory cytokines, chemokines and cell adhesion factors, thereby inducing inflammation. Secukinumab, a human anti-human IL-17A monoclonal antibody, is used as a therapeutic drug for psoriasis vulgaris and psoriasis arthropathica. In addition, IL-17A is reportedly involved in autoimmune diseases such as rheumatoid arthritis, multiple sclerosis and inflammatory bowel disorder, various cancers including non-small-cell lung cancer, colorectal cancer and pancreatic cancer, arteriosclerosis, etc. Therefore, vaccines capable of inducing an anti-IL-17A antibody are expected to treat these IL-17A-associated diseases.

The epitope of human IL-17A used for an OSK-1-IL-17A conjugate is not particularly limited as long as it is an epitope capable of inducing the production of an antibody that inhibits the functions of IL-17A (neutralizing antibody). Preferable examples of the epitope include peptides consisting of any of the following amino acid sequences.

RSSDYYNR (SEQ ID NO: 10)

PKRSSDYYNRSTSPW (SEQ ID NO: 11)

CPNSEDKNFPR (SEQ ID NO: 29)

RNEDPERYPS (SEQ ID NO: 30)

-continued (SEQ ID NO: 31)
NRSTSPW (SEQ ID NO: 32)
LHRNEDP (SEQ ID NO: 33)
RYPSVIWEA (SEQ ID NO: 34)
PKRSSDYYNR (SEQ ID NO: 35)
INPKRSSDYYNR (SEQ ID NO: 36)
ININPKRSSDYYNR The accession numbers of the amino acid sequence of human IL-17A and the nucleotide sequence of the gene encoding human IL-17A are NP_002181 (NCBI) and NM_002190 (NCBI), respectively.

Peptides which consist of an amino acid sequence that is the same as the amino acid sequence of any of SEQ ID NOs: 10, 11 and 29 to 36 except for 1 or 2 amino acid deletions, substitutions or additions and which are capable of inducing the production of an antibody that inhibits the functions of IL-17A are also preferable as the epitope of human IL-17A used for the OSK-1-IL-17A conjugate. Moreover, a peptide consisting of a partial sequence containing the amino acid sequence of residues 3 to 10 of SEQ ID NO: 11 is also preferable as the epitope of human IL-17A used for the OSK-1-IL-17A conjugate.

Allergy is caused by specific substances (allergens), and after an allergen enters the body, the immune system responds to the allergen and induces IgE production. The produced IgE antibodies are attached to mast cells and basophils and maintained on the surface of these cells. When the same allergen enters the body again, IgE and the allergen bind together, thereby inducing the release of chemical mediators such as histamine and leukotriene, which trigger allergic symptoms. In the case where an allergy to a specific allergen has developed, overproduction of specific IgE against the allergen deteriorates allergic symptoms. Allergic symptoms can be alleviated by inhibiting or abolishing the actions of IgE, and for example, the anti-human IgE antibody omalizumab is used for the treatment of bronchial asthma. Therefore, vaccines capable of inducing an anti-IgE antibody are expected to treat allergic diseases such as bronchial asthma, pollen allergy, allergic conjunctivitis and atopic dermatitis.

The epitope of human IgE used for an OSK-1-IgE conjugate is not particularly limited as long as it is an epitope capable of inducing the production of an antibody that inhibits the functions of IgE (neutralizing antibody). A preferable example of the epitope is a peptide consisting of the following amino acid sequence.

YQCRVTHPHLP (SEQ ID NO: 12)

The accession numbers of the amino acid sequence of the constant region of a human immunoglobulin e chain and the nucleotide sequence of the gene encoding the constant region of a human immunoglobulin a chain are P01854 (UniProtKB) and NG_001019 (NCBI), respectively.

Peptides which consist of an amino acid sequence that is the same as the amino acid sequence of SEQ ID NO: 12 except for 1 or 2 amino acid deletions, substitutions or additions and which are capable of inducing the production of an antibody that inhibits the functions of IgE are also preferable as the epitope of human IgE used for the OSK-1-IgE conjugate.

S100 proteins are a family of calcium-binding proteins with two EF-hand domains and are cell type-specifically expressed. So far, 20 subfamilies have been identified. S100A9 (also referred to as MRP14) is a low-molecular-weight calcium-binding S100 protein and is known to be involved in various inflammatory diseases. In addition, elevated levels of serum S100A9 are observed in patients of many inflammatory diseases including giant cell arteritis, cystic fibrosis, rheumatoid arthritis, dermatosis, chronic inflammatory bowel disease, chronic bronchitis, some malignant tumors and autoimmune disease. Moreover, blocking of S100A9 reportedly could prevent thrombus formation without increasing the risk of hemorrhage. Therefore, vaccines capable of inducing an anti-S100A9 antibody are expected to prevent thrombus formation in atherothrombosis, myocardial infarction and cerebral infarction.

The epitope of human S100A9 used for an OSK-1-S100A9 conjugate is not particularly limited as long as it is an epitope capable of inducing the production of an antibody that inhibits the functions of S100A9 (neutralizing antibody). A preferable example of the epitope is a peptide consisting of the following amino acid sequence.

GHHHKPGLGE (SEQ ID NO: 13)

The accession numbers of the amino acid sequence of human S100A9 and the nucleotide sequence of the gene encoding human S100A9 are NP_002956 (NCBI) and NM_002965 (NCBI), respectively.

Peptides which consist of an amino acid sequence that is the same as the amino acid sequence of SEQ ID NO: 13 except for 1 or 2 amino acid deletions, substitutions or additions and which are capable of inducing the production of an antibody that inhibits the functions of S100A9 are also preferable as the epitope of human S100A9 used for the OSK-1-S100A9 conjugate.

PCSK9 (proprotein convertase subtilisin/kexin type 9) was identified as a causative gene of familial hypercholesterolemia. Subsequent studies confirmed that PCSK9 degrades LDL receptors expressed on the surface of hepatocytes and reduces the ability of the liver to take up LDL-C from the blood. By inhibiting the functions of PCSK9, the degradation of LDL receptors can be prevented and the uptake of blood cholesterol into the liver can be facilitated, thus enabling the reduction of the blood cholesterol level. For example, the anti-human PCSK9 monoclonal antibody evolocumab is used for the treatment of familial hypercholesterolemia and hypercholesterolemia, and RNAi drugs that inhibit the functions of PCSK9 have been developed. Therefore, vaccines capable of inducing an anti-PCSK9 antibody are expected to treat hypercholesterolemia.

The epitope of human PCSK9 used for an OSK-1-PCSK9 conjugate is not particularly limited as long as it is an epitope capable of inducing the production of an antibody that inhibits the functions of PCSK9 (neutralizing antibody). Preferable examples of the epitope include peptides consisting of any of the following amino acid sequences.

(SEQ ID NO: 14)
LRPRGQPNQC (SEQ ID NO: 15)
SRHLAQASQ

-continued (SEQ ID NO: 16)
SRSGKRRGER

The accession numbers of the amino acid sequence of human PCSK9 and the nucleotide sequence of the gene encoding human PCSK9 are NP_777596 (NCBI) and NM_174936 (NCBI), respectively.

Peptides which consist of an amino acid sequence that is the same as the amino acid sequence of any of SEQ ID NOs: 14 to 16 except for 1 or 2 amino acid deletions, substitutions or additions and which are capable of inducing the production of an antibody that inhibits the functions of PCSK9 are also preferable as the epitope of human PCSK9 used for the OSK-1-PCSK9 conjugate.

In the case where experiments using laboratory animals (mice etc.) are performed to examine the effect of the vaccine of the present invention, it is preferable to use an epitope sequence of the laboratory animal corresponding to the above-mentioned human epitope sequence. The epitope sequence of the laboratory animal to be used can be designed by alignment of the amino acid sequence of a target protein obtained from known databases (NCBI etc.) with the corresponding human amino acid sequence. Table 1 lists the mouse epitope sequences corresponding to the above-mentioned human epitope sequences of SEQ ID NOs: 2 to 16.

the full-length amino acid sequence of human IgE is based on the amino acid sequence registered with the accession number P01854, the full-length amino acid sequence of mouse IgE is based on the amino acid sequence registered with the accession number P06336, the full-length amino acid sequence of human S100A9 is based on the amino acid sequence registered with the accession number NP_002956, the full-length amino acid sequence of mouse S100A9 is based on the amino acid sequence registered with the accession number CAC14292, the full-length amino acid sequence of human PCSK9 is based on the amino acid sequence registered with the accession number NP_777596, and the full-length amino acid sequence of mouse PCSK9 is based on the amino acid sequence registered with the accession number NP_705793.

The length of the epitope of the biological protein used for the vaccine of the present invention is not particularly limited, but the length is preferably 20 amino acids or less, more preferably 15 amino acids or less, still more preferably 13 amino acids or less, yet still more preferably 12 amino acids or less, yet still more preferably 11 amino acids or less, and yet still more preferably 10 amino acids or less. The minimum of the length is not particularly limited, but the length is preferably 3 amino acids or more, more preferably 4 amino acids or more, still more preferably 5 amino acids or more, and still more preferably 6 amino acids or more.

TABLE 1

| Target protein | Mouse epitope sequence | Positions in full-length amino acid sequence | Human epitope sequence | Positions in full-length amino acid sequence |
|---|---|---|---|---|
| DPP4 | ENSTFESFG (SEQ ID NO: 17) | 89-97 | ENSTFDEFG (SEQ ID NO: 2) | 91-99 |
| | NKRQLITEE (SEQ ID NO: 3) | 132-140 | NKRQLITEE (SEQ ID NO: 3) | 138-146 |
| | KSTFRVKSYS (SEQ ID NO: 18) | 48-57 | KNTYRLKLYS (SEQ ID NO: 4) | 50-59 |
| | YSDESLQYPK (SEQ ID NO: 5) | 235-244 | YSDESLQYPK (SEQ ID NO: 5) | 241-250 |
| | PPHFDKSKKY (SEQ ID NO: 6) | 525-534 | PPHFDKSKKY (SEQ ID NO: 6) | 531-540 |
| | GLPPEDNLD (SEQ ID NO: 19) | 666-675 | GLPTPEDNLD (SEQ ID NO: 7) | 672-681 |
| | FSKEAKYYQ (SEQ ID NO: 8) | 455-463 | FSKEAKYY (SEQ ID NO: 8) | 461-469 |
| | NSSIFLENSTFESFG (SEQ ID NO: 20) | 83-97 | NSSVFLENSTFDEFG (SEQ ID NO: 9) | 85-99 |
| IL-17A | RPSDYLNR (SEQ ID NO: 21) | 65-72 | RSSDYYNR (SEQ ID NO: 10) | 62-69 |
| | SRRPSDYLNRSTSPW (SEQ ID NO: 22) | 63-77 | PKRSSDYYNRSTSPW (SEQ ID NO: 11) | 60-74 |
| | CPNTEAKDFLQ (SEQ ID NO: 37) | 35-45 | CPNSEDKNFPR (SEQ ID NO: 29) | 33-43 |
| | RNEDPDRYPS (SEQ ID NO: 38) | 81-90 | RNEDPERYPS (SEQ ID NO: 30) | 78-87 |
| | NRSTSPW (SEQ ID NO: 31) | 71-77 | NRSTSPW (SEQ ID NO: 31) | 68-74 |
| | LHRNEDP (SEQ ID NO: 32) | 79-85 | LHRNEDP (SEQ ID NO: 32) | 76-82 |
| | YPSVIWEA (SEQ ID NO: 33) | 87-95 | RYPSVIWEA (SEQ ID NO: 33) | 84-92 |
| | RYPSDYLNR (SEQ ID NO: 39) | 63-72 | PKRSSDYYNR (SEQ ID NO: 34) | 60-69 |
| | VSSRRPSDYLNR (SEQ ID NO: 40) | 61-72 | TNPKRSSDYYNR (SEQ ID NO: 35) | 58-69 |
| | AKVSSRRPSDYLNR (SEQ ID NO: 41) | 59-72 | TNTNPKRSSDYYNR (SEQ ID NO: 36) | 56-69 |
| IgE | YQCIVDHPDFP (SEQ ID NO: 23) | 283-293 | YQCRVTHPHLP (SEQ ID NO: 12) | 297-307 |
| PCSK9 | PALRSRRQPG (SEQ ID NO: 25) | 580-589 | LRPRGQPNQC (SEQ ID NO: 14) | 580-589 |
| | CRSRPSAKA (SEQ ID NO: 26) | 682-690 | SRHLAQASQ (SEQ ID NO: 15) | 682-690 |
| | SFSRSGRRRG (SEQ ID NO: 27) | 491-500 | SRSGKRRGER (SEQ ID NO: 16) | 491-500 |
| S100A9 | GHSHGKGCGK (SEQ ID NO: 24) | 104-113 | GHHHKPGLGE (SEQ ID NO: 13) | 102-111 |

In Table 1, the full-length amino acid sequence of human DPP4 is based on the amino acid sequence registered with the accession number NP_001926, the full-length amino acid sequence of mouse DPP4 is based on the amino acid sequence registered with the accession number AAH22183, the full-length amino acid sequence of human IL-17A is based on the amino acid sequence registered with the accession number NP_002181, the full-length amino acid sequence of mouse IL-17A is based on the amino acid sequence registered with the accession number NP_034682, In the complex of the OSK-1 peptide and the epitope of the biological protein, the OSK-1 peptide and the epitope may be conjugated directly or via a linker (used as a synonym for a spacer). The linker is not particularly limited as long as it is capable of connecting the OSK-1 peptide with the epitope of the biological protein. Examples of the linker include aminocarboxylic acids such as β-aminoalanine, γ-aminobutyric acid, ε-aminocaproic acid, 7-aminoheptanoic acid, 12-aminolauric acid, glutamic acid and p-aminobenzoic acid. Other examples include L-amino acids, which are present in naturally occurring proteins, and D-isomers thereof. In Examples of the present specification, ε-aminocaproic acid is used, but is a non-limiting example.

The sequential order of the OSK-1 peptide and the epitope of the biological protein in the complex is not particularly limited. The complex may have the OSK-1 peptide at the N-terminal side and the epitope of the biological protein at the C-terminal side. Also, the complex may have the epitope of the biological protein at the N-terminal side and the OSK-1 peptide at the C-terminal side. Preferably, the complex has the OSK-1 peptide at the N-terminal side and the epitope of the biological protein at the C-terminal side.

In the complex, the amino acid at the N-terminus is preferably acetylated. In the complex, the amino acid at the C-terminus is preferably amidated. More preferably, the amino acid at the N-terminus of the complex is acetylated, and the amino acid at the C-terminus of the complex is amidated.

The complex of the OSK-1 peptide and the epitope of the biological protein can be prepared as a fusion protein. For example, the complex can be prepared by using known genetic engineering techniques, specifically by preparing a fusion gene encoding a fusion protein of the OSK-1 peptide and the epitope of the biological protein, constructing a recombinant expression vector having the fusion gene expressibly inserted, transfecting the recombinant expression vector into appropriate host cells for expression of a recombinant protein, and purifying the recombinant protein. Alternatively, the preparation of the complex of the OSK-1 peptide and the epitope of the biological protein can be performed using the above-described fusion gene in combination with a known in vitro coupled transcription-translation system (for example, a cell-free protein synthesis system derived from rabbit reticulocytes, wheat germ or *Escherichia coli*). Moreover, in the case where a bacteriophage is used to provide the expression of the complex of the OSK-1 peptide and the epitope of the biological protein as a recombinant protein on the surface of the bacteriophage, the complex expressed on the phage surface may be directly administered to a target animal without isolation or purification.

The complex of the OSK-1 peptide and the epitope of the biological protein can be produced by a solid phase synthesis method (e.g., the Fmoc method and the Boc method) or a liquid phase synthesis method according to a known ordinary peptide synthesis protocol. In the case where the complex has the OSK-1 peptide directly conjugated to the epitope of the biological protein, or in the case where the complex has the OSK-1 peptide conjugated to the epitope of the biological protein via an appropriate amino acid(s), the whole complex can be synthesized. Alternatively, the OSK-1 peptide and the epitope of the biological protein may be synthesized separately before coupling of the two peptides via an appropriate linker.

The linker can be introduced by a well-known method used in peptide synthesis chemistry. Firstly, a peptide fragment whose N-terminal end is supposed to be coupled to a linker is produced by a standard method. Then, an aminocarboxylic acid as the linker, in which the amino group is appropriately protected, and the peptide fragment are condensed in standard conditions using a condensing agent used in peptide synthesis chemistry. After removal of the protective group for the linker group, the desired amino acid is introduced at the next position. An example of such a method is the solid phase peptide synthesis method often employed in a peptide automatic synthesizer. Examples of the protective group for the aminocarboxylic acid used in such a procedure include a tBOC (tert-butyl oxy carbonyl) group and an FMOC (fluorenyl-methoxy-carbonyl) group. Examples of the condensing agent include carbodiimide compounds such as DCC (N,N'-dicyclohexylcarbodiimide) and EDC (N-(3-dimethylaminopropyl)-N'-ethylcarbodiimide); imidazole compounds such as CDI (1,1'-carbonyldiimidazole); phosphonium salt compounds such as BOP (benzotriazol-1-yloxytris(dimethylamino)phosphonium hexafluorophosphate); and uronium salt compounds such as HBTU (O-(benzotriazol-1-yl)-N,N,N',N'-tetramethyluronium hexafluorophosphate) and HCTU (O-(6-chlorobenzotriazol-1-yl)-N,N,N',N'-tetramethyluronium hexafluorophosphate). Also, a desired conjugate can be obtained by another procedure using an appropriate combination of the above conditions. Specifically, first, a specific peptide fragment of OSK-1 and a peptide fragment of the epitope sequence of the target biological protein are separately produced and appropriately protected. Next, these fragments are condensed with an appropriately protected linker group and then deprotected in appropriate conditions.

Without an adjuvant, the vaccine of the present invention can induce an antibody that inhibits the functions of the disease-causing biological protein, and therefore is highly useful. However, the vaccine of the present invention may contain one or more adjuvants. In the case where the vaccine of the present invention contains an adjuvant, the adjuvant can be selected as appropriate from known adjuvants. Specific examples of the known adjuvants include aluminum adjuvants (for example, aluminum salts such as aluminum hydroxide, aluminum phosphate and aluminum sulfate, or any combination thereof), complete or incomplete Freund's adjuvant, TLR ligands (for example, CpG, Poly(I:C), Pam3CSK4, etc.), BAY, DC-chol, pcpp, monophosphoryl lipid A, QS-21, cholera toxin and formylmethionyl peptides. Preferable adjuvants are aluminum adjuvants, TLR ligands and a combination of these. In the case where the vaccine of the present invention contains an adjuvant, the amount of the adjuvant is not particularly limited and can be selected as appropriate according to the kind of the adjuvant etc. For example, in the case where an aluminum adjuvant (aluminum hydroxide) and CpG are used in combination, it is preferable that the vaccine contains an about 1- to 100-fold amount of the aluminum adjuvant and an about 1- to 50-fold amount of CpG relative to the amount of the fusion protein of the present invention on a mass basis.

The vaccine of the present invention can be administered orally or parenterally. Examples of the parenteral administration include intraperitoneal administration, subcutaneous administration, intracutaneous administration, intramuscular administration, intravenous administration, intranasal administration, transdermal administration, transmucosal administration, sublingual administration and inhalation administration. Preferred is parenteral administration, and more preferred are intracutaneous administration, subcutaneous administration and intramuscular administration. For parenteral administration, microneedle injection, non-needle injection, a stamping method, etc. may be employed.

For the formulation of the vaccine of the present invention, the complex of the OSK-1 peptide and the epitope of the biological protein, a pharmaceutically acceptable carrier and if needed an additive are blended and formed into a dosage form. Specific examples of the dosage form include oral preparations such as tablets, coated tablets, pills, powders, granules, capsules, solutions, suspensions and emulsions; and parenteral preparations such as injections, infusions, suppositories, ointments and patches. The amount of the carrier or the additive to be used is determined as appropriate based on the range of amount conventionally used in the pharmaceutical field. The carrier or the additive that can be used is not particularly limited, and examples include various carriers such as water, physiological saline, other aqueous solvents, and aqueous or oily bases; and various additives such as excipients, binders, pH adjusters, disintegrants, absorption enhancers, lubricants, colorants, corrigents and fragrances.

Examples of the additive used for solid oral preparations include excipients such as lactose, mannitol, glucose, microcrystalline cellulose and corn starch; binders such as hydroxypropyl cellulose, polyvinylpyrrolidone and magnesium aluminometasilicate; dispersants such as corn starch; disintegrants such as calcium carboxymethyl cellulose; lubricants such as magnesium stearate; solubilizing agents such as glutamic acid and aspartic acid; stabilizers; water soluble polymers including celluloses such as hydroxypropyl cellulose, hydroxypropylmethyl cellulose and methyl cellulose, and synthetic polymers such as polyethylene glycol, polyvinylpyrrolidone and polyvinyl alcohol; sweeteners such as white sugar, powder sugar, sucrose, fructose, glucose, lactose, reduced malt sugar syrup (maltitol syrup), reduced malt sugar syrup powder (maltitol syrup powder), high-glucose corn syrup, high-fructose corn syrup, honey, sorbitol, maltitol, mannitol, xylitol, erythritol, aspartame, saccharin and saccharin sodium; and coating agents such as white sugar, gelatin, hydroxypropyl cellulose and hydroxypropylmethyl cellulose phthalate.

The formulation of liquid oral preparations involves dissolution, suspension or emulsification in a generally used diluent. Examples of the diluent include purified water, ethanol and a mixture thereof. The oral liquid preparations may further contain a wetting agent, a suspending agent, an emulsifier, a sweetener, a flavoring agent, a fragrance, a preservative, a buffering agent and/or the like.

Examples of the additive used for injections for parenteral administration include isotonizing agents such as sodium chloride, potassium chloride, glycerin, mannitol, sorbitol, boric acid, borax, glucose and propylene glycol; buffering agents such as a phosphate buffer solution, an acetate buffer solution, a borate buffer solution, a carbonate buffer solution, a citrate buffer solution, a Tris buffer solution, a glutamate buffer solution and an ε-aminocaproate buffer solution; preservatives such as methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, disodium edetate, boric acid and borax; thickeners such as hydroxyethyl cellulose, hydroxypropyl cellulose, polyvinyl alcohol and polyethylene glycol; stabilizers such as sodium hydrogen sulfite, sodium thiosulfate, disodium edetate, sodium citrate, ascorbic acid and dibutylhydroxytoluene; and pH adjusters such as hydrochloric acid, sodium hydroxide, phosphoric acid and acetic acid. The injection may further contain an appropriate solubilizer. Examples of the solubilizer include alcohols such as ethanol; polyalcohols such as propylene glycol and polyethylene glycol; and nonionic surfactants such as polysorbate 80, polyoxyethylene hydrogenated castor oil 50, lysolecithin and Pluronic polyol. Liquid preparations such as injections can be preserved in a frozen state, or in a dried state after water removal by lyophilization etc. Lyophilized preparations can be reconstituted in distilled water for injection or the like just before use.

The vaccine of the present invention can be administered to any animal (a human or a non-human animal) with an immune system. Examples of the animal include mammals such as humans, monkeys, cattle, horses, pigs, sheep, goats, dogs, cats, guinea pigs, rats and mice; and birds such as chickens, ducks and geese. The vaccine of the present invention is useful as a veterinary drug, but is preferably used for human children and human adults.

In the administration of the vaccine of the present invention, the dosing frequency and interval are not particularly limited. For example, the vaccine may be administered once, or multiple times at intervals of about two days to about eight weeks. The dose of the vaccine varies with the administration subject, the administration method, etc., but the dose per administration is preferably about 0.01 μg to about 10 mg, more preferably about 0.1 μg to about 1 mg, and still more preferably about 1 μg to about 0.1 mg.

The present invention includes a method for preventing or treating a disease caused by a target biological protein, the method comprising administering an effective amount of the vaccine of the present invention to an animal.

Further, the present invention includes the vaccine of the present invention for use in prevention or treatment of a disease caused by the biological protein.

Moreover, the present invention includes use of the vaccine of the present invention for production of a medicament for prevention or treatment of a disease caused by the biological protein.

OSK-1, which is used as the carrier protein for the epitope of the disease-causing biological protein in the vaccine of the present invention, is a peptide of 20 amino acids with a very low antigenicity. Therefore, OSK-1 is less likely to cause unfavorable effects and side effects attributable to the carrier protein per se. In spite of its short length, OSK-1 has a strong adjuvant effect, and therefore is capable of imparting the vaccine with an effective capability of inducing antibody production. Moreover, the complex of OSK-1 and the epitope of the biological protein is capable of inducing the production of not only Th2-type antibodies such as IgG1, but also a large amount of Th1-type antibodies such as IgG2a, IgG2b and IgG3. Therefore, the complex is less likely to cause side effects such as allergic reactions and is very useful. Furthermore, in the case where carrier proteins from natural source, such as KLH, are used, their impurities may post a problem, but OSK-1 is free from such a problem because OSK-1 can be produced by chemical synthesis. Furthermore, the short peptide OSK-1 is advantageous in terms of reduced production cost.

EXAMPLES

Hereinafter, the present invention will be illustrated in detail by examples, but the present invention is not limited thereto.

Production Example of Peptide

A protected peptide-bound resin was synthesized by the Fmoc method using a fully-automatic solid-phase synthesizer according to the protocol described in: Solid Phase Peptide Synthesis, Pierce (1984); Fmoc Solid Synthesis: A Practical Approach, Oxford University Press (2000); The Fifth Series of Experimental Chemistry (Jikken Kagaku Kouza), vol. 16, Synthesis of Organic Compounds IV; or the like. To the protected peptide-bound resin, trifluoroacetic acid (TFA) and a scavenger (a mixture of thioanisole, ethanedithiol, phenol, triisopropylsilane, water and the like) were added for cleavage of the protected peptide from the resin and deprotection thereof. Thus, the peptide of interest was obtained as a crude product. For the purification of the peptide, the crude product was applied to a reverse-phase HPLC column (ODS) and elution was performed with a gradient of 0.1% TFA-$H_2O/CH_3CN$. The fractions containing the peptide of interest were combined and freeze-dried, and the peptide of interest was obtained. The amino acid sequence of the synthesized peptide was confirmed with the amino acid sequencer G1000A (Hewlett Packard), PPSQ-23A (Shimadzu Corporation) or Procise cLC (ABI). The obtained peptide was subjected to N-terminal acetylation.

Example 1: Examination of Antibody Production Induced by OSK-1-DPP4 Conjugate—Part 1

An OSK-1-DPP4 conjugate composed of an OSK-1 peptide (SEQ ID NO: 1) conjugated to a mouse DPP4 epitope peptide (SEQ ID NO: 17) via an ε-Acp linker (Ac-ELKLIFLHRLKRLRKRLKRK-X-ENSTFESFG (X=ε-Acp)) was assessed for the antibody production-inducing effect. For this test, the following two groups were prepared: a physiological saline group and an OSK-1-DPP4 conjugate group (100 μg/mouse) (6 animals per group). Test samples were intracutaneously administered to Balb/c mice 3 times at 2-week intervals. Before the first administration and every 2 weeks until 8 weeks after the first administration, blood samples were collected, and the antibody titer against the DPP4 epitope peptide was measured by ELISA.

The results are shown in FIG. 1. After the administration of the OSK-1-DPP4 conjugate, antibody production against the DPP4 epitope peptide was observed.

Example 2: Examination of Antibody Production Induced by OSK-1-DPP4 Conjugate—Part 2

The antibody production-inducing effect of the same OSK-1-DPP4 conjugate as used in Example 1 was compared with that of a conjugate of KLH (keyhole limpet hemocyanin) and the mouse DPP4 epitope peptide (SEQ ID NO: 17) (KLH-DPP4). For this test, the following three groups were prepared: a KLH-DPP4 conjugate group (20 μg/mouse), an OSK-1-DPP4 conjugate group (100 μg/mouse) and an OSK-1-DPP4 conjugate (100 μg/mouse) plus Alum (Alhydrogel 2% (InvivoGen) 1 mg/mouse) group (2 animals per group). Test samples were intracutaneously administered to Balb/c mice 3 times at 2-week intervals. Before the first administration, every 2 weeks until 6 weeks after the first administration, and 12 weeks after the first administration, blood samples were collected, and the antibody titer against the DPP4 epitope peptide was measured by ELISA.

Figure 2:
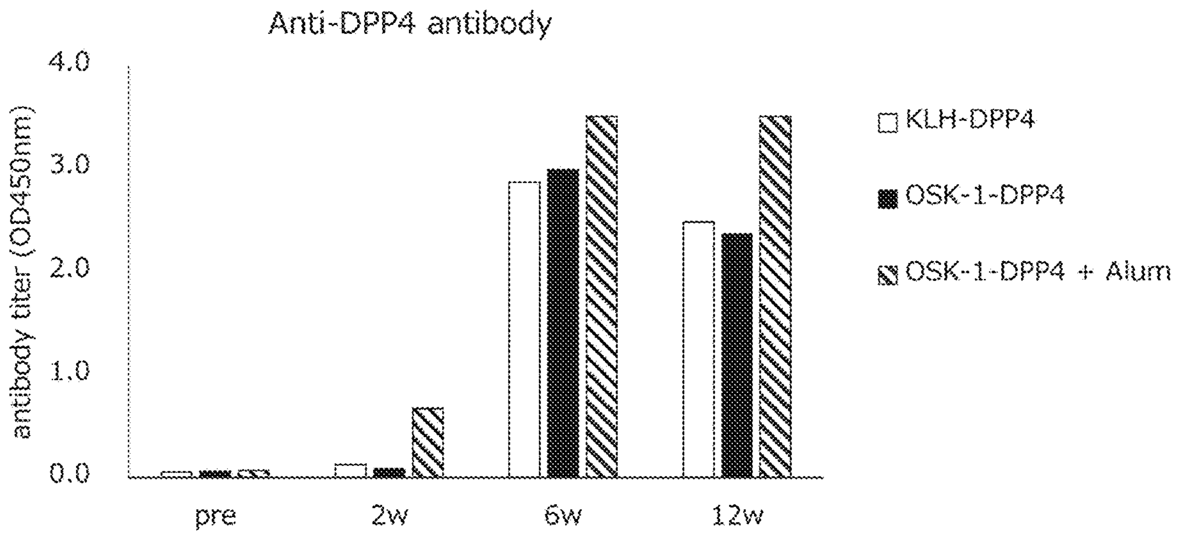
FIG. 2 shows the comparison of the antibody production-inducing effects of the OSK-1-DPP4 conjugate and a conjugate of KLH and a mouse DPP4 epitope peptide (SEQ ID NO: 17) (KLH-DPP4).

The results are shown in FIG. 2. The antibody production-inducing capability of the OSK-1-DPP4 conjugate was comparable to that of the KLH-DPP4 conjugate. In addition, synergistic effect was observed in the OSK-1-DPP4 conjugate plus Alum group.

Example 3: Analysis of IgG Subclass of Produced Antibodies

The IgG subclass of antibodies produced by vaccination with the same OSK-1-DPP4 conjugate as used in Examples 1 and 2 was compared with that of antibodies produced by vaccination with the same KLH-DPP4 conjugate as used in Example 2. For this test, the following three groups were prepared: an OSK-1-DPP4 conjugate group (100 μg/mouse), a KLH-DPP4 conjugate (20 μg/mouse) plus Alum (Alhydrogel 2% (InvivoGen) 1 mg/mouse) group and a KLH-DPP4 conjugate (20 μg/mouse) plus OSK-1 (100 μg/mouse) group. Test samples were intracutaneously administered to Balb/c mice 3 times at 2-week intervals and at 9 weeks after the start of the administration, 4 times in total. At 11 weeks after the start of the administration, blood samples were collected, and the titer of each IgG subclass of antibodies against the DPP4 epitope peptide was measured by ELISA.

Figure 3:
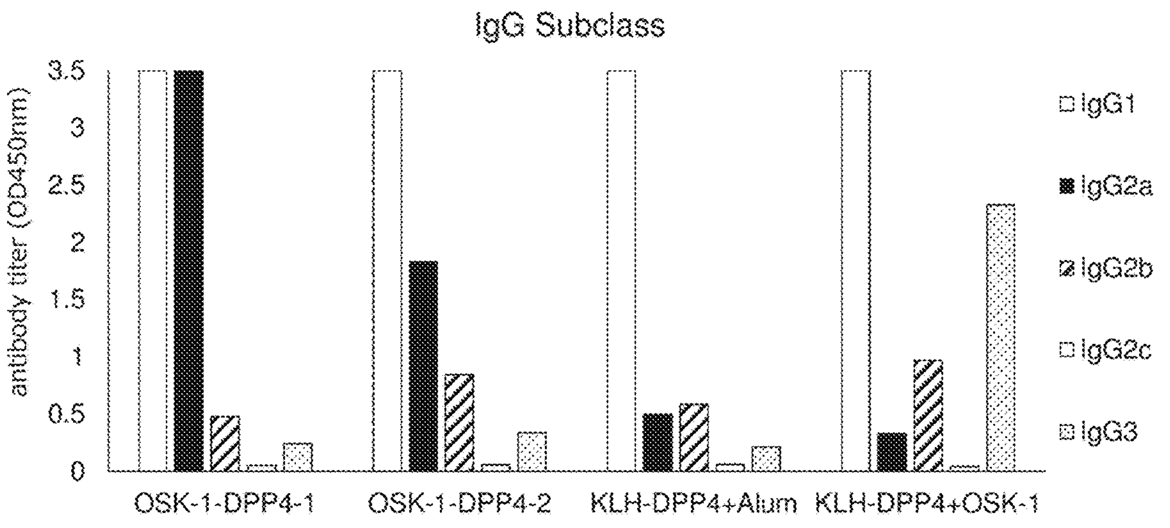
FIG. 3 shows the results of the analysis of the IgG subclass of antibodies produced by vaccination with the OSK-1-DPP4 conjugate in comparison with a KLH-DPP4 conjugate plus Alum group and a KLH-DPP4 conjugate plus OSK-1 group.

The results are shown in FIG. 3. In the KLH-DPP4 conjugate plus Alum group, the titer of IgG1, which is a Th2-type IgG subclass, had a tendency to be particularly higher than those of other IgG subclasses. In the OSK-1-DPP4 conjugate group, IgG2a and IgG2b, which are Th1-type IgG subclasses, were also produced at high levels in addition to IgG1. Similarly, in the KLH-DPP4 conjugate plus OSK-1 group, the titers of IgG2b and IgG3, which are Th1-type IgG subclasses, were high.

Reference Example 1: Examination of Antitumor Effect of OSK-1-WT1 Conjugate—Part 1

An OSK-1-WT1 conjugate composed of the OSK-1 peptide (SEQ ID NO: 1) conjugated to a WT1 peptide (SEQ ID NO: 28) via an ε-Acp linker (Ac-ELKLIFLHRLKRLRKRLKRK-X-RMFPNAPYL (X=ε-Acp)) was assessed for the antitumor effect. In addition, the adjuvant effect of the OSK-1 peptide on the antitumor effect of a WT1 peptide vaccine was also examined. For this test, the following four groups were prepared: a physiological saline group, a WT1 peptide (100 μg/mouse) plus poly(I:C) (InvivoGen; Poly(I:C) HMW VacciGrade, 50 μg/mouse) group, a WT1 peptide (100 μg/mouse) plus OSK-1 peptide (100 μg/mouse) group and an OSK-1-WT1 conjugate (350 μg/mouse) group (6 animals per group). The vaccines were administered to C57BL/6J mice once a week, 4 times in total. One week after the 4th administration, B16F10 melanoma cells ($1\times10^5$ cells/mouse) were implanted into the dorsal skin. The vaccines were administered again one week after the cell implantation. The body weight and the diameter of the tumor were measured twice a week after the cell implantation. The diameter of the tumor was measured using a digital caliper, and the tumor volume was calculated by the formula: (major axis)×(minor axis)$^2$.

Figure 4:
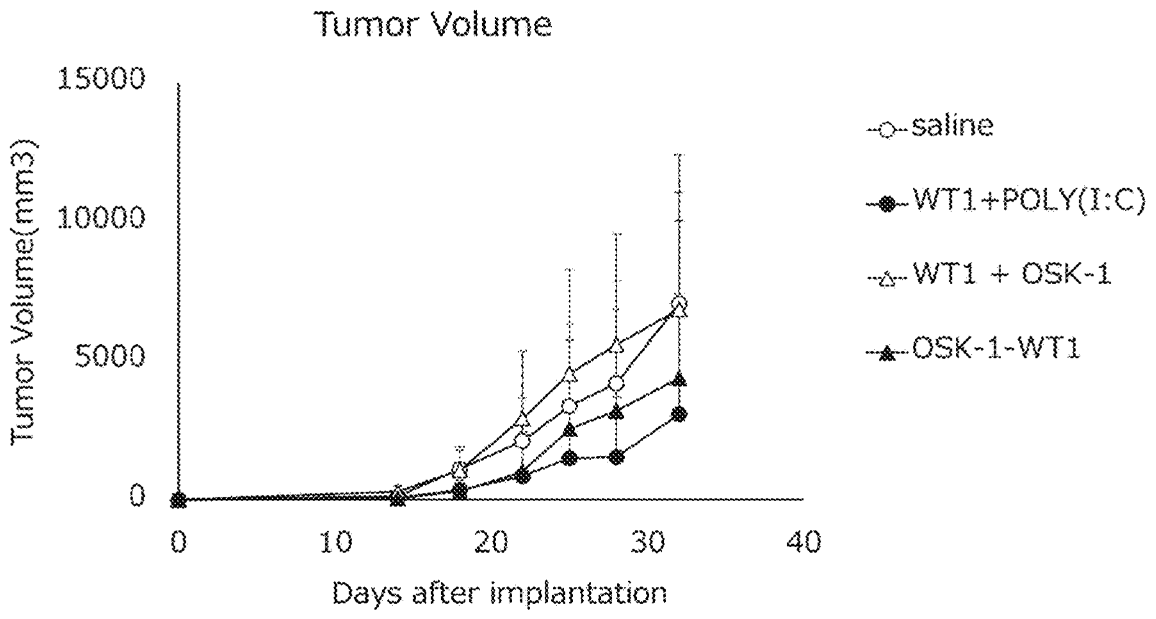
FIG. 4 shows the antitumor growth effect of an OSK-1-WT1 conjugate composed of the OSK-1 peptide (SEQ ID NO: 1) conjugated to a WT1 peptide (SEQ ID NO: 28) via an ε-Acp linker in mice having undergone vaccination with the OSK-1-WT1 conjugate followed by subcutaneous implantation of cancer cells.
Figure 5:
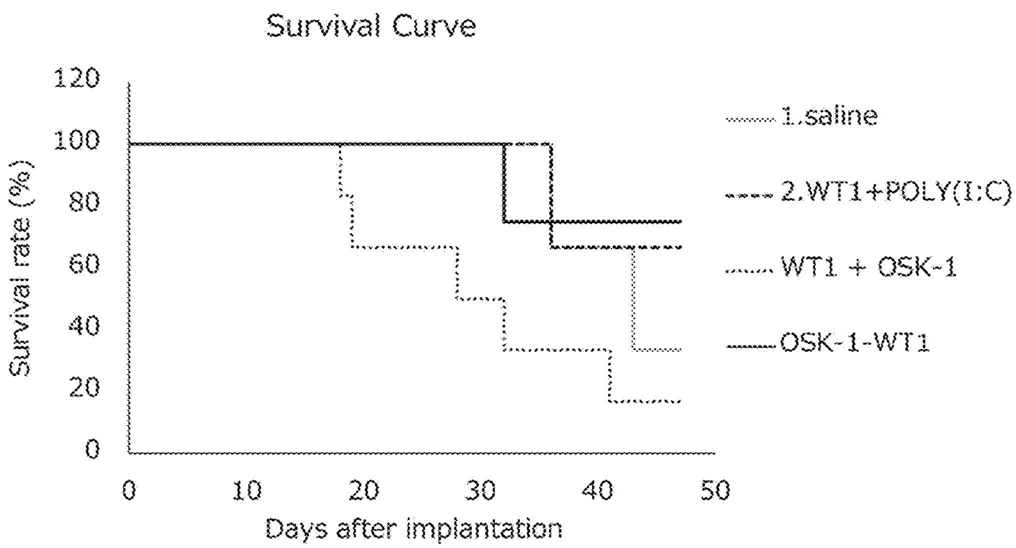
FIG. 5 shows the survival benefit of the OSK-1-WT1 conjugate in mice having undergone vaccination with the OSK-1-WT1 conjugate followed by subcutaneous implantation of cancer cells.

The results of the tumor volume are shown in FIG. 4, and the results of the survival rate are shown in FIG. 5. In the group where the WT1 peptide vaccine was administered in combination with the OSK-1 peptide as the adjuvant, neither the inhibitory effect on tumor growth nor the survival benefit was observed. In contrast, in the OSK-1-WT1 conjugate group, the inhibitory effect on tumor growth and the survival benefit were observed.

Reference Example 2: Examination of Antitumor Effect of OSK-1-WT1 Conjugate—Part 2

The antitumor effect of the same OSK-1-WT1 conjugate as used in Reference Example 1 was assessed. For this test, the following four groups were prepared: a physiological saline group, a WT1 peptide (100 μg/mouse) plus poly(I:C) (InvivoGen; Poly (I:C) HMW VacciGrade, 50 μg/mouse) group, an OSK-1-WT1 conjugate (350 μg/mouse) group and a cisplatin (5 mg/kg) group (10 animals per group). B16F10 melanoma cells ($3\times10^5$ cells/mouse) were implanted to C57BL/6J mice, and at the same day, the vaccines were intracutaneously administered into the dorsal skin. The day of cell implantation was designated as Day 0. The vaccines were administered on Day 7, Day 14, Day 21, Day 28 and Day 35. Twice a week after the cell implantation, the diameter of the tumor was measured using a digital caliper, and the tumor volume was calculated by the formula: (major axis)×(minor axis)$^2$.

Figure 6:
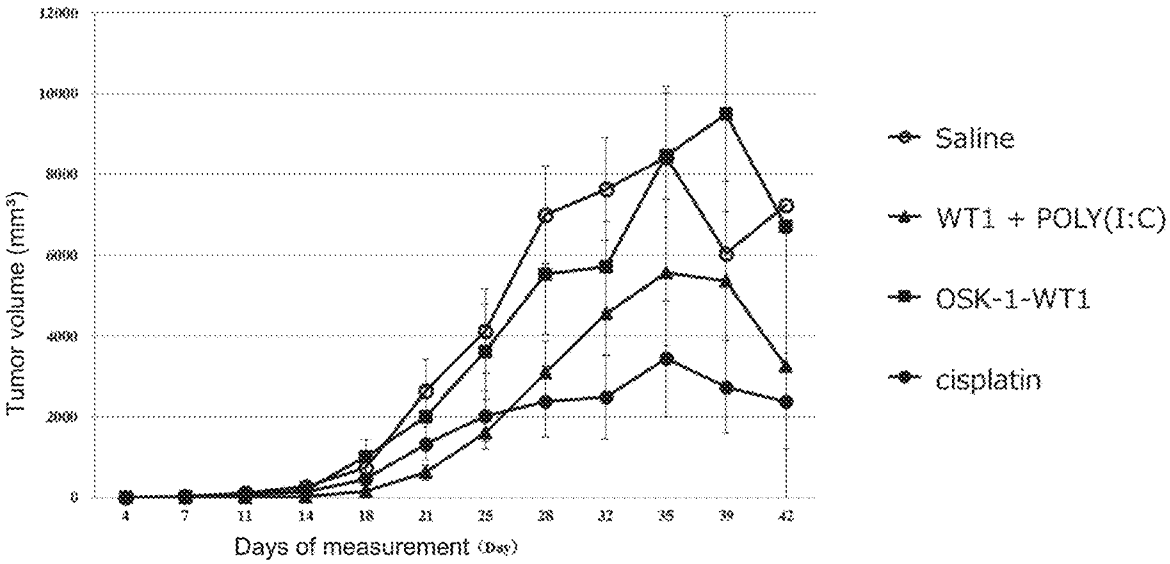
FIG. 6 shows the antitumor growth effect of the OSK-1-WT1 conjugate in mice having undergone subcutaneous implantation of cancer cells and the first vaccination with the OSK-1-WT1 conjugate on the same day.
Figure 7:
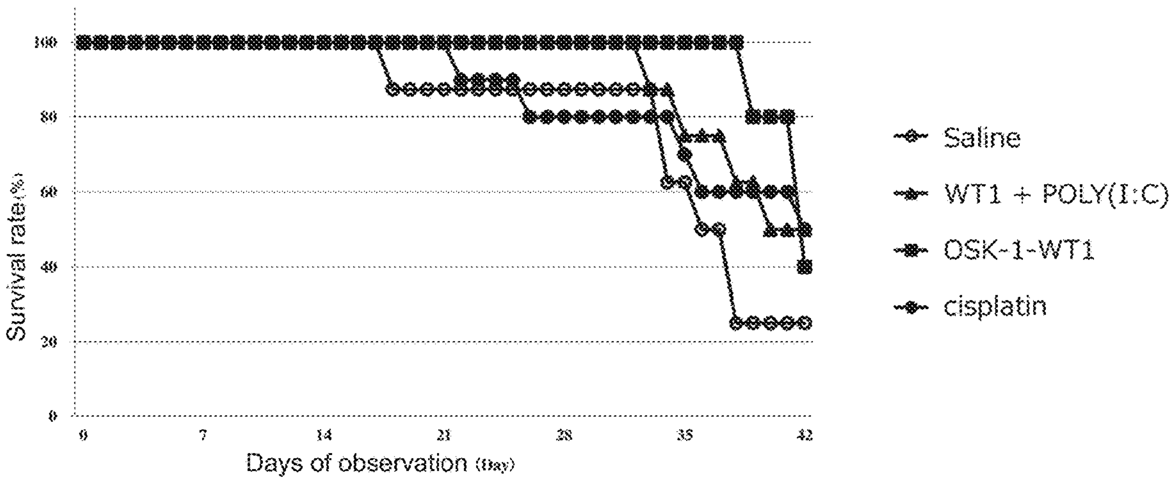
FIG. 7 shows the survival benefit of the OSK-1-WT1 conjugate in mice having undergone subcutaneous implantation of cancer cells and the first vaccination with the OSK-1-WT1 conjugate on the same day.

The results of the tumor volume are shown in FIG. 6, and the results of the survival rate are shown in FIG. 7. In the case where vaccination started on the day of cell implantation, the inhibitory effect of the OSK-1-WT1 conjugate on tumor growth was modest, but the tumor volume was kept at lower levels than that of the physiological saline administration group (negative control) until Day 32. In addition, the survival benefit in the OSK-1-WT1 conjugate group was comparable to those in the WT1 peptide plus poly(I:C) group and the cisplatin group.

Example 4: Examination of Antibody Production Induced by OSK-1-DPP4 Conjugates—Part 3

Seven types of mouse DPP4 epitope peptides (SEQ ID NOs: 3, 5, 6, 8, 18, 19 and 20) and one type of human DPP4 epitope peptide (SEQ ID NO: 9) were separately conjugated to the OSK-1 peptide (SEQ ID NO: 1) via an ε-Acp linker to produce 8 types of OSK-1-DPP4 conjugates. Hereinafter, each OSK-1-DPP4 conjugate is referred to as "OSK1-DDP4-sequence ID number".

Six types of OSK-1-DPP4 conjugates containing different mouse DPP4 epitope peptides (SEQ ID NOs: 3, 5, 6, 8, 18 and 19) were intracutaneously administered to Balb/c mice at a dose of 100 μg per animal 3 times at 2-week intervals. Before the first administration and every 2 weeks after the first administration, blood samples were collected, and the antibody titer against each epitope peptide was measured by ELISA.

The antibody titers measured 4 weeks after the first administration are shown in Table 2. The antibody titer is expressed as a half maximum value. The half maximum value is a value of a dilution factor at which the absorbance of the serum sample is half of the maximum absorbance measured in a measurement device. The half maximum value can be obtained from a sigmoid curve created by plotting serum dilution factors against measured absorbances.

TABLE 2

| DPP4 vaccine Half Maximum | | |
|---|---|---|
| ID | Dose (μg) | Half Maximum(4 W) |
| OSK1-DPP4-3 | 100 | <10 |
| OSK1-DPP4-18 | 100 | <10 |
| OSK1-DPP4-5 | 100 | 20.8 |
| OSK1-DPP4-6 | 100 | 248.3 |
| OSK1-DPP4-19 | 100 | 97.7 |
| OSK1-DPP4-8 | 100 | <10 |

Three types of OSK-1-DPP4 conjugates, OSK1-DDP4-6, OSK1-DDP4-9 and OSK1-DDP4-12, were intracutaneously administered to Balb/c mice at a dose of 250 μg per animal 3 times at 2-week intervals. At 4, 9 and 13 weeks after the first administration, blood samples were collected, and the antibody titer against each epitope peptide was measured by ELISA.

The results are shown in Table 3. The antibody titer is expressed as a half maximum value.

TABLE 3

| DPP4 vaccine Half Maximum 2 | | | | |
|---|---|---|---|---|
| ID | Dose (μg) | 4 w | 9 w | 13 w |
| OSK1-DPP4-6 | 250 | 329.4 | 280.3 | 408.6 |
| OSK1-DPP4-9 | 250 | <10 | <10 | 53.6 |
| OSK1-DPP4-20 | 250 | <10 | 10.4 | 44.9 |

Example 5: Assessment of OSK-1-DPP4 Conjugate by HbA1c Level Measurement

An OSK-1-DPP4 conjugate composed of the OSK-1 peptide (SEQ ID NO: 1) conjugated to the DPP4 epitope peptide (SEQ ID NO: 6) via an ε-Acp linker was intracutaneously administered at a dose of 100 μg per animal 3 times at 2-week intervals to Balb/c mice which had been given free access to a high fat diet (DIO SERIES DIET D12492, CLEA Japan). At 57 days after the first administration, blood samples were collected, and as quickly as possible, each of the blood samples was partly transferred to a separate EDTA-containing tube. Each tube was inverted for mixing, and EDTA-treated blood samples were prepared. About 20 μL of each EDTA-treated blood sample was transferred to a microtube for HbA1c measurement, and the HbA1c level was measured using Quo-Lab HbA1c Analyzer (Nipro). The results show that the HbA1c level (%, NGSP) of the OSK-1-DPP4 conjugate group was improved (reduced by 0.4%) as compared with that of the control group (KLH administration group).

Example 6: Assessment of OSK-1-DPP4 Conjugates by Oral Glucose Tolerance Test (OGTT)

Two types of OSK-1-DPP4 conjugates composed of the OSK-1 peptide (SEQ ID NO: 1) conjugated to the DPP4 epitope peptide (SEQ ID NO: 6 or 9) via an ε-Acp linker were intracutaneously administered at a dose of 250 μg per animal 3 times at 2-week intervals to Balb/c mice which had been given free access to a high fat diet (DIO SERIES DIET D12492, CLEA Japan). The OSK-1-DPP4 conjugates were further intracutaneously administered at a dose of 250 μg per animal at 63 days after the first administration. An oral glucose tolerance test (OGTT) was performed at 77 days after the first administration. The mice were under fasting conditions for about 16 hours before the OGTT test, and during the OGTT test, the mice were still under fasting conditions. A 20% glucose solution was orally administered at a single dose of 5 mL/kg to the mice. Blood collection and blood glucose level measurement were performed under unanesthetized conditions. The mouse tail was gently cut with a razor blade, and the glucose concentration in the blood leaking from the cut was measured with a blood glucose monitoring system (Nipro, FreeStyle Freedom). The blood glucose levels were measured before glucose loading and at 30, 60, 90 and 120 minutes after glucose loading, at 5 time points in total. The blood glucose levels of each group were plotted against time, and the blood glucose area under the curve (glucose AUC) (time*mg/dl) was calculated. The results show that the AUCs of both the OSK-1-DPP4 conjugate administration groups were lower than that of the control group (KLH administration group).

Example 7: Examination of IgE Production Induced by OSK-1-DPP4 Conjugate

In terms of IgE production against a target protein, OSK1-DPP4-17 was compared with KLH-DPP4-17, which used KLH as a carrier protein instead of OSK1. To a KLH-DPP4-17 group of mice, KLH-DPP4-17 and Alum (Alhydrogel 2% (InvivoGen)) were intracutaneously administered as a mixture at doses of 20 μg/mouse and 1 mg/mouse, respectively. To an OSK-1-DPP4-17 group of mice, OSK-1-DPP4-17 was intracutaneously administered at a dose of 100 μg/mouse. In either group, the conjugate was intracutaneously administered to Balb/c mice 3 times at 2-week intervals, and the 4th administration was performed at 11 weeks after the first administration. At 21 weeks after the first administration, blood samples were collected, and the amount of serum IgE antibody against DPP4 was measured by ELISA.

Figure 8:
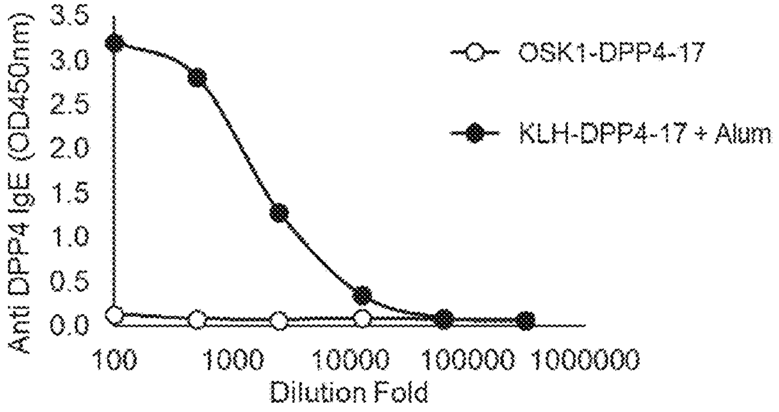
FIG. 8 shows the comparison of OSK-1-DPP4 conjugate-induced IgE production against a target protein with KLH-DPP4 conjugate-induced IgE production against the target protein.

The results are shown in FIG. 8. IgE production against the target protein was observed in the KLH-DPP4-17 group, but no IgE production against the target protein was observed in the OSK1-DPP4-17 group.

Example 8: Examination of Antibody Production Induced by OSK-1-IL-17A Conjugates (1) Production of OSK-1-IL-17A Conjugates Ten types of mouse IL-17A epitope peptides (SEQ ID NOs: 21, 22, 31 to 33 and 37 to 41) were separately conjugated to the OSK-1 peptide (SEQ ID NO: 1) via an ε-Acp linker to produce 10 types of OSK-1-IL-17A conjugates. Hereinafter, each OSK-1-IL-17A conjugate is referred to as "OSK1-IL-sequence ID number". FIGS. 9 to 12 show (A) the results of amino acid analysis and (B) the results of HPLC analysis of representative 4 types of conjugates containing different epitope peptides (SEQ ID NOs: 21, 31, 32 and 40). The results of the analyses of the other conjugates were substantially the same as these results.

(2) Measurement of Antibody Titer

Ten types of OSK-1-IL-17A conjugates were intracutaneously administered to Balb/c mice at the doses indicated in Table 4 three times at 2-week intervals. Before the first administration and every 2 weeks until 6 weeks after the first administration, blood samples were collected, and the antibody titer against each epitope peptide was measured by ELISA.

Figure 13:
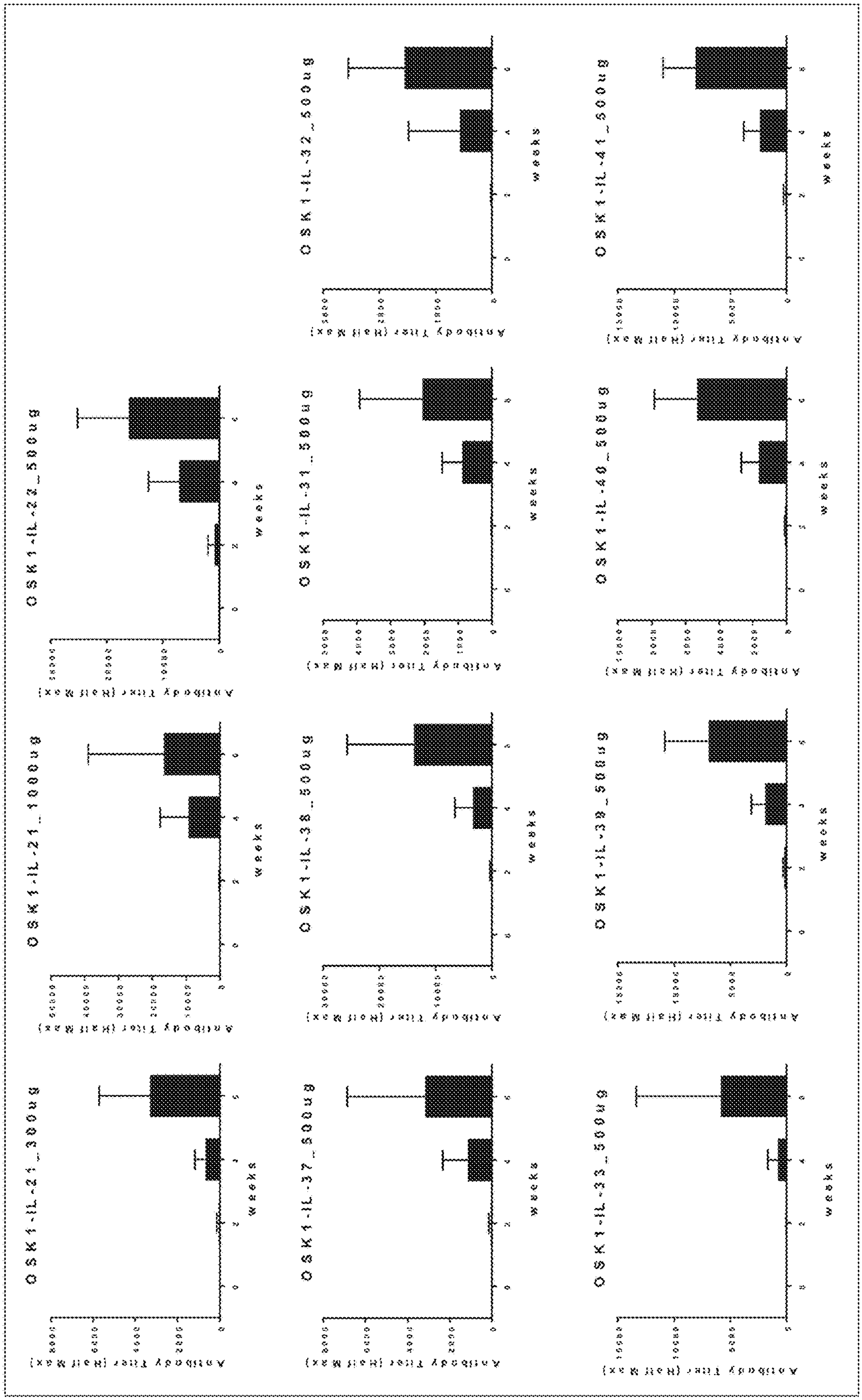
FIG. 13 shows the antibody production-inducing effect of OSK-1-IL-17A conjugates.

The results obtained 6 weeks after the first administration are shown in Table 4. The antibody titers measured 2, 4 and 6 weeks after the first administration are shown in FIG. 13. The antibody titer is expressed as a half maximum value.

TABLE 4

| IL-17 vaccine Half Maximum | | |
|---|---|---|
| ID | Dose | Half Maximum(6 W) |
| OSK1-IL-21 | 300 μg | 3282.2 |
| OSK1-IL-21 | 1000 μg | 16484.1 |
| OSK1-IL-22 | 500 μg | 16050.1 |
| OSK1-IL-37 | 500 μg | 3190.8 |
| OSK1-IL-38 | 500 μg | 13909.2 |
| OSK1-IL-31 | 500 μg | 2067.7 |
| OSK1-IL-32 | 500 μg | 1559.4 |
| OSK1-IL-33 | 500 μg | 5859.0 |
| OSK1-IL-39 | 500 μg | 6954.8 |
| OSK1-IL-40 | 500 μg | 5323.0 |
| OSK1-IL-41 | 500 μg | 8097.8 |

Example 9: Assessment of OSK-1-IL-17A Conjugates in Model Mice of Imiquimod-Induced Psoriasiform Dermatitis—Part 1

A model of psoriasiform dermatitis induced by imiquimod was used as a psoriasis model. Three types of OSK-1-IL-17A conjugates (OSK1-IL-31, OSK1-IL-32 and OSK1-IL-40) were intracutaneously administered to 6-week-old BALB/c mice at a dose of 500 μg per animal 3 times at 2-week intervals. At 2 weeks after the 3rd vaccination, the dorsal skin was shaved and depilated with a depilatory cream. To the denuded skin, Beselna Cream 5% (trade name, Mochida Pharmaceutical Co., LTD.) was applied at a daily dose of 62.5 mg of imiquimod for 8 days for psoriasis induction. To the ears, Beselna Cream 5% was applied at a daily dose of 0.35 mg of imiquimod per ear for 8 days for psoriasis induction.

Figure 14:
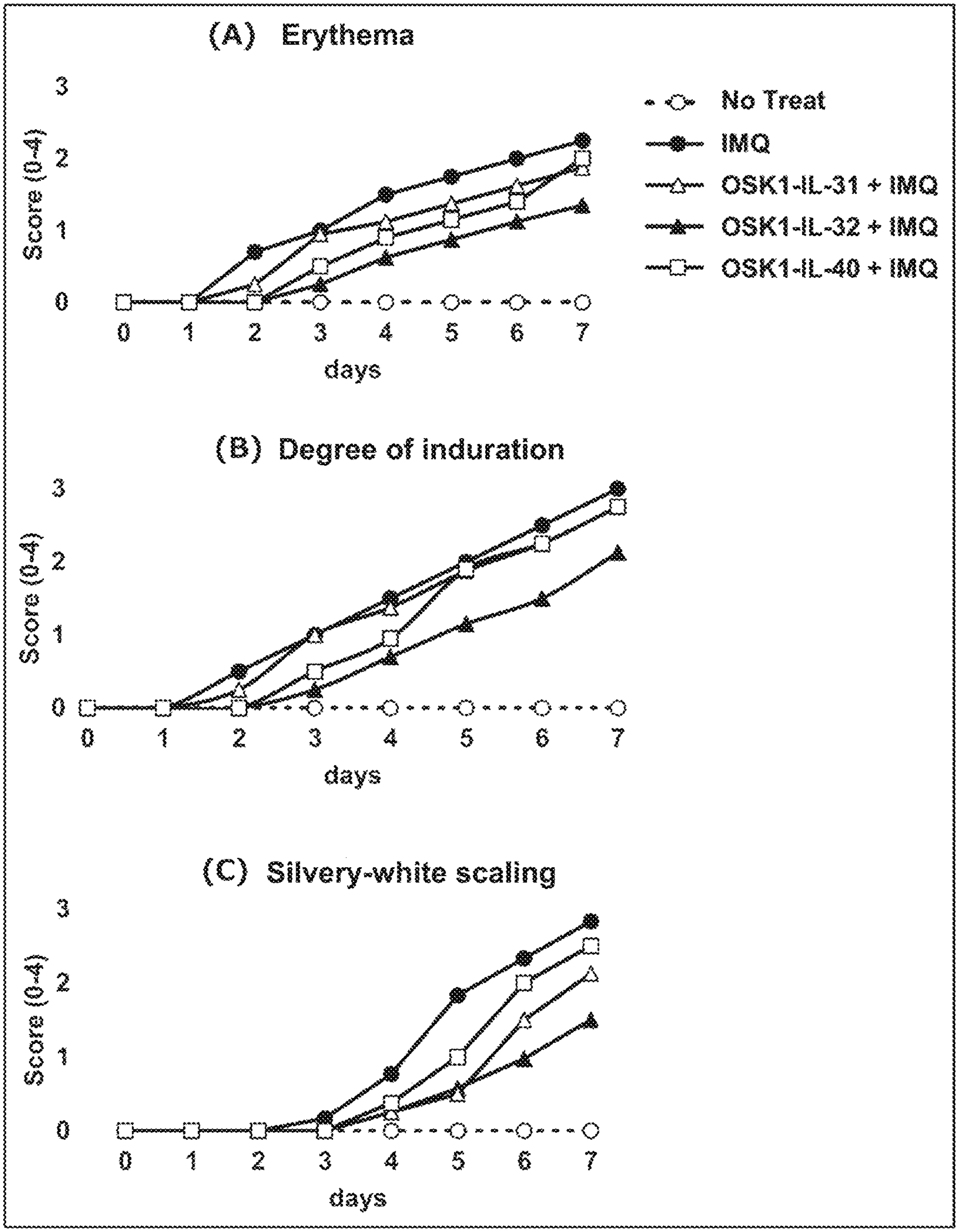
FIG. 14 shows the results of the assessment of the medical efficacy of OSK-1-IL-17A conjugates based on the skin conditions of model mice of imiquimod-induced psoriasiform dermatitis.
Figure 15:
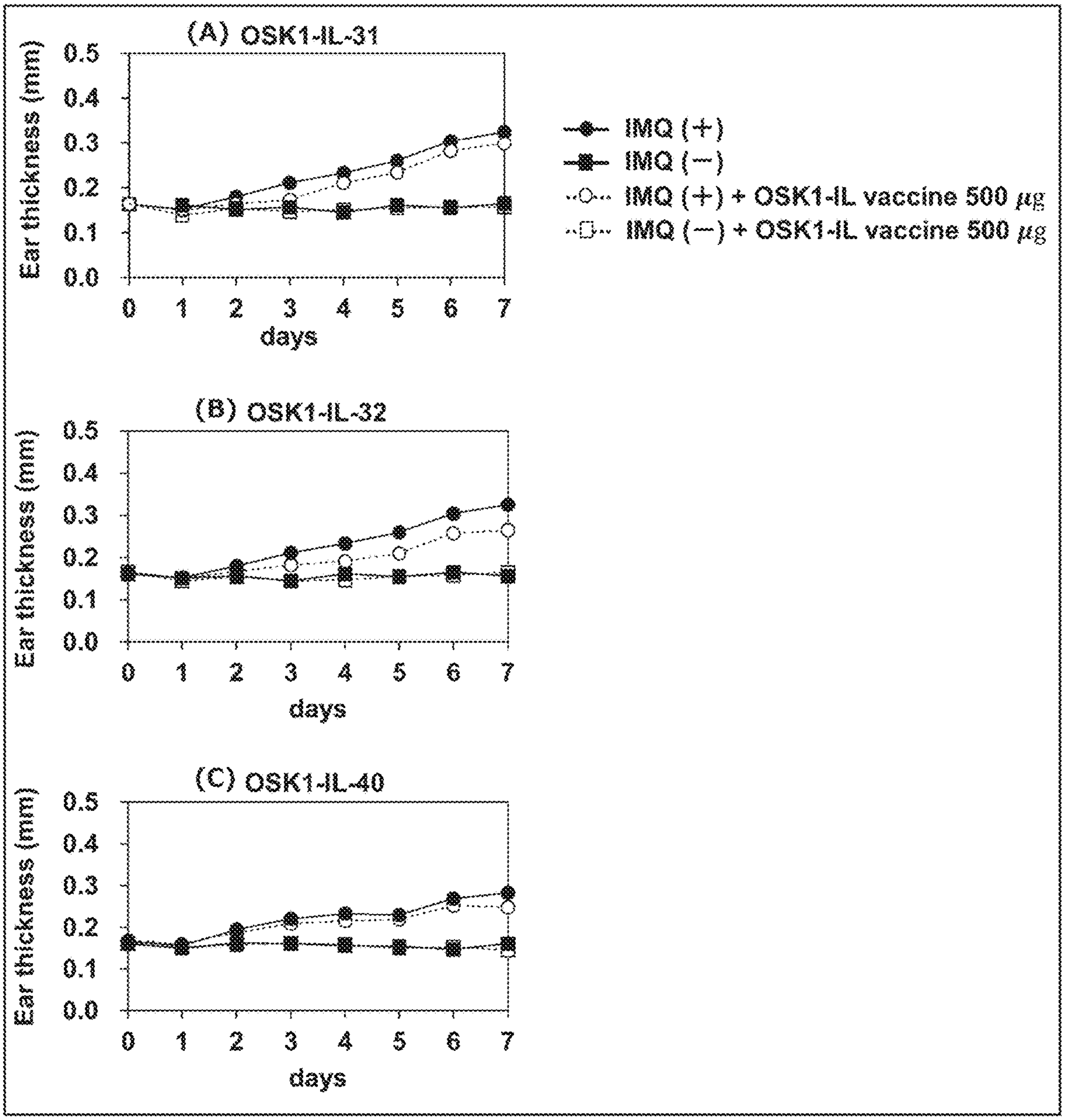
FIG. 15 shows the results of the assessment of the medical efficacy of the OSK-1-IL-17A conjugates based on the ear thickness of model mice of imiquimod-induced psoriasiform dermatitis.

The skin conditions (erythema, the degree of induration, the area of skin covered with silvery-white scale) were observed daily for 8 days from the start of psoriasis induction (Day 0 to Day 7), and scored on a 5-point scale of 0 to 4 (0: none, 1: mild, 2: moderate, 3: severe and 4: very severe) for assessment. The ear thickness was measured daily for 8 days from the start of psoriasis induction (Day 0 to Day 7) using a digital caliper. The results of the skin conditions are shown in FIG. 14, and the results of the ear thickness are shown in FIG. 15. The results show that the four types of OSK-1-IL-17A conjugates alleviate imiquimod-induced psoriasiform dermatitis.

Example 10: Assessment of OSK-1-IL-17A Conjugate in Model Mice of Imiquimod-Induced Psoriasiform Dermatitis—Part 2

(1) Skin Condition and Ear Thickness

OSK1-IL-21, which is an OSK-1-IL-17A conjugate, was intracutaneously administered to Balb/c mice at a dose of 100 μg, 300 μg or 1000 μg per animal 3 times at 2-week intervals. Separately, KLH-IL-21, which used KLH as a carrier protein instead of OSK-1, was intracutaneously administered to Balb/c mice at a dose of 20 μg per animal 3 times at 2-week intervals. For the administration of KLH-IL-21, a mixture of KLH-IL-21 with Freund's complete adjuvant (SIGMA) at 50 μL/mouse was used at the first administration, and a mixture of KLH-IL-21 with Freund's incomplete adjuvant (SIGMA) at 50 μL/mouse was used at the second and third administrations. The procedures were the same as used in Example 9 shown above except that the different vaccine was used and that Beselna Cream 5% was applied daily for 13 days.

Figure 16:
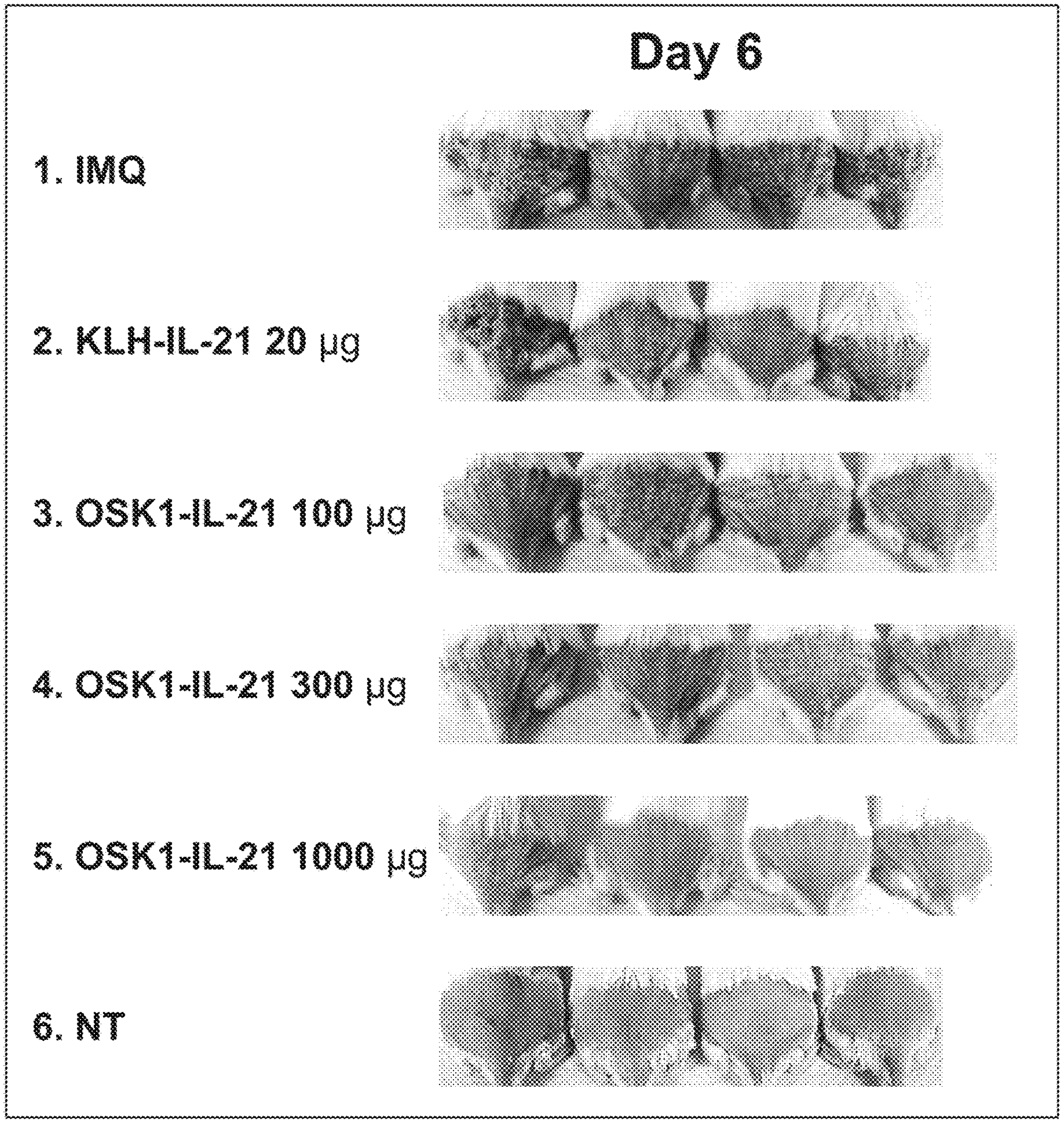
FIG. 16 shows the skin conditions of model mice of imiquimod-induced psoriasiform dermatitis on Day 6 after the start of psoriasis induction preceded by vaccination with an OSK-1-IL-17A conjugate or a KLH-IL-17A conjugate.
Figure 17:
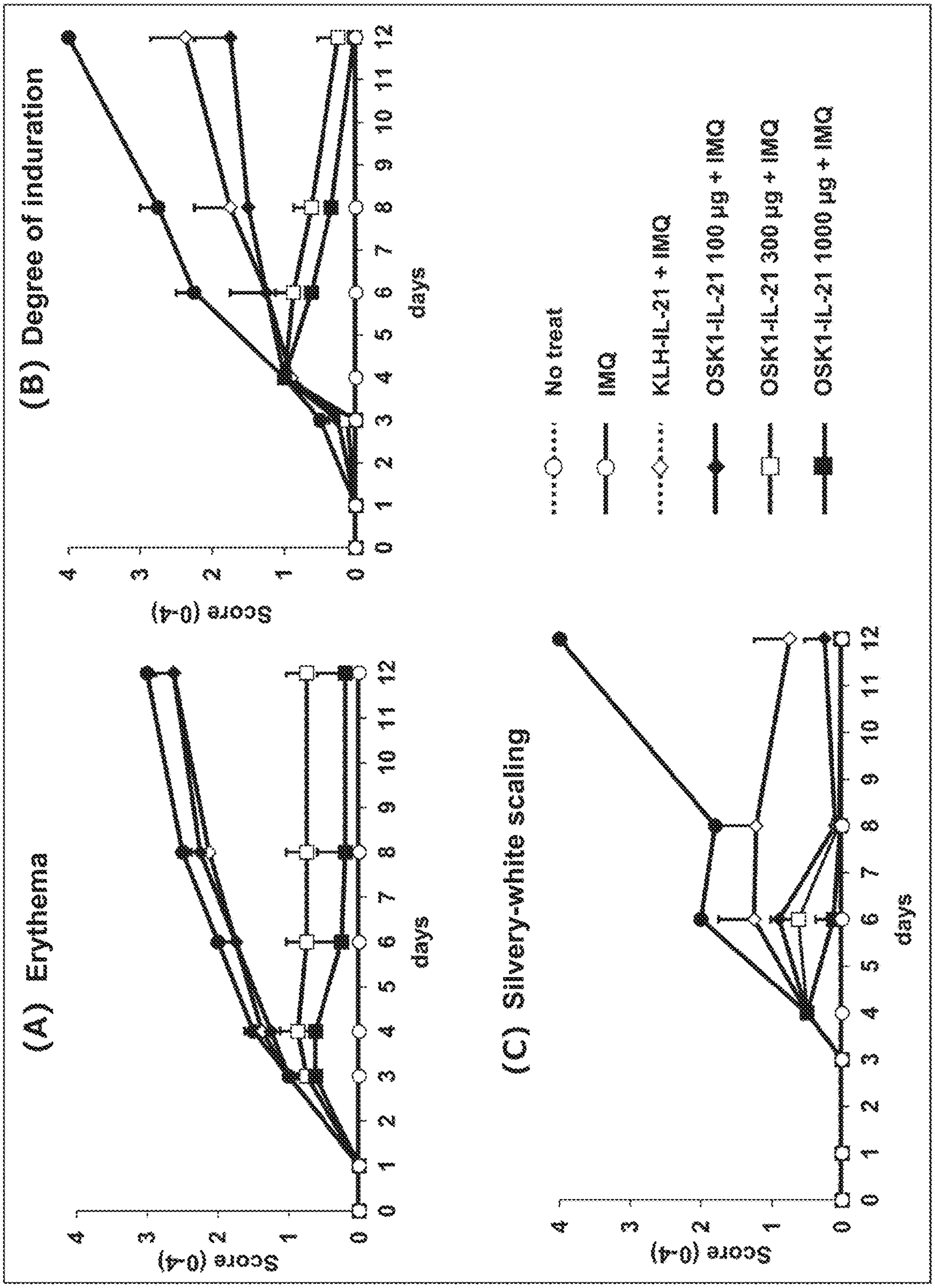
FIG. 17 shows the comparison of the medical efficacies of the OSK-1-IL-17A conjugate and the KLH-IL-17A conjugate based on the skin conditions of model mice of imiquimod-induced psoriasiform dermatitis.
Figure 18:
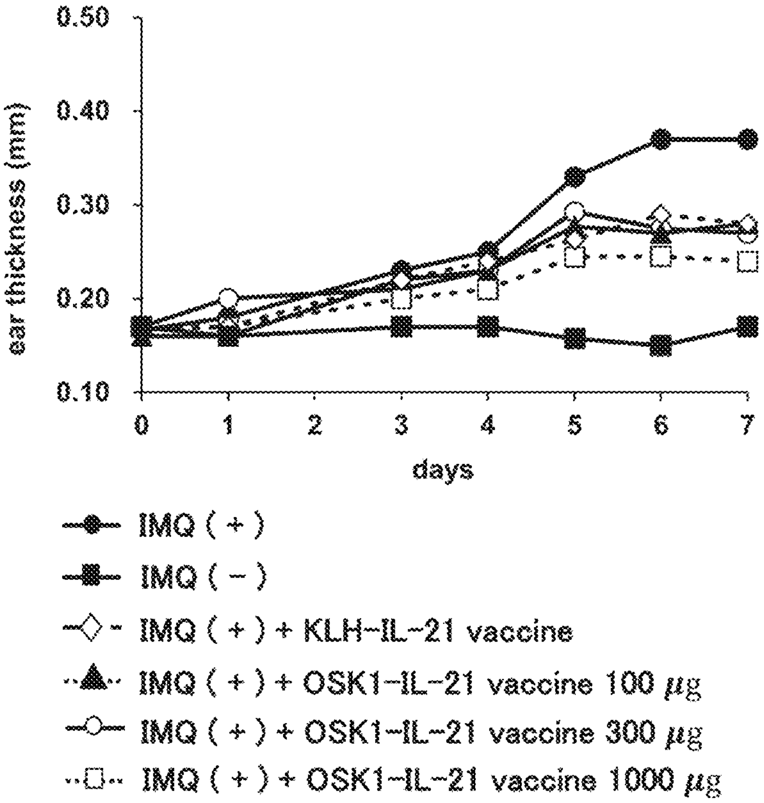
FIG. 18 shows the comparison of the medical efficacies of the OSK-1-IL-17A conjugate and the KLH-IL-17A conjugate based on the ear thickness of model mice of imiquimod-induced psoriasiform dermatitis.

Photographs of skin conditions on Day 6 after the start of psoriasis induction are shown in FIG. 16. Changes in the skin conditions during the period of psoriasiform dermatitis induction (Day 0 to Day 12) are shown in FIG. 17, and changes in the ear thickness during the period of psoriasiform dermatitis induction (Day 0 to Day 7) are shown in FIG. 18. The results show that the OSK-1-IL-17A conjugate is capable of more potently alleviating imiquimod-induced psoriasiform dermatitis than the KLH-IL-17A conjugate.

(2) Immunohistochemical Staining

After the induction of psoriasiform dermatitis by application of imiquimod, immune cells present in the skin and involucrin expression in the skin were detected by immunohistochemical staining.

On Day 12 after the start of psoriasis induction, the dorsal skin and the auricles were dissected, fixed with 4% PFA, and embedded in paraffin. After section preparation, deparaffinization and antigen retrieval treatment were performed. Then, the sections were blocked to prevent nonspecific reaction, reacted with a primary antibody, and reacted with a labeled secondary antibody. The sections were stained for involucrin, which is the final marker of keratinization, to examine the degree of keratinization. The sections were also stained for the macrophage marker F4/80 and the granulocyte marker Gr-1 to detect immune cells.

Figure 19:
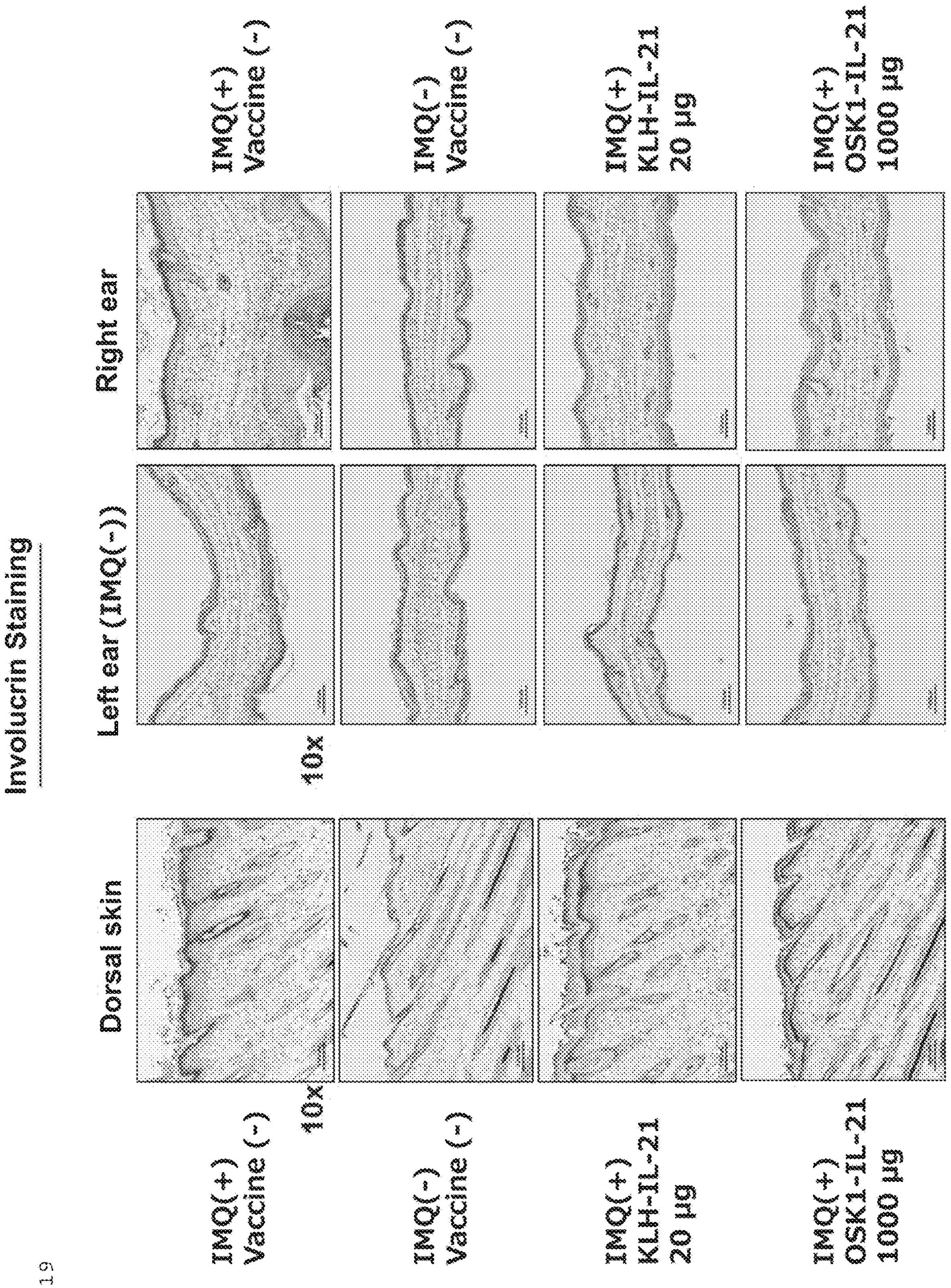
FIG. 19 shows the results of involucrin staining of the skin of model mice of imiquimod-induced psoriasiform dermatitis on Day 12 after the start of psoriasis induction preceded by vaccination with the OSK-1-IL-17A conjugate or the KLH-IL-17A conjugate.
Figure 20:
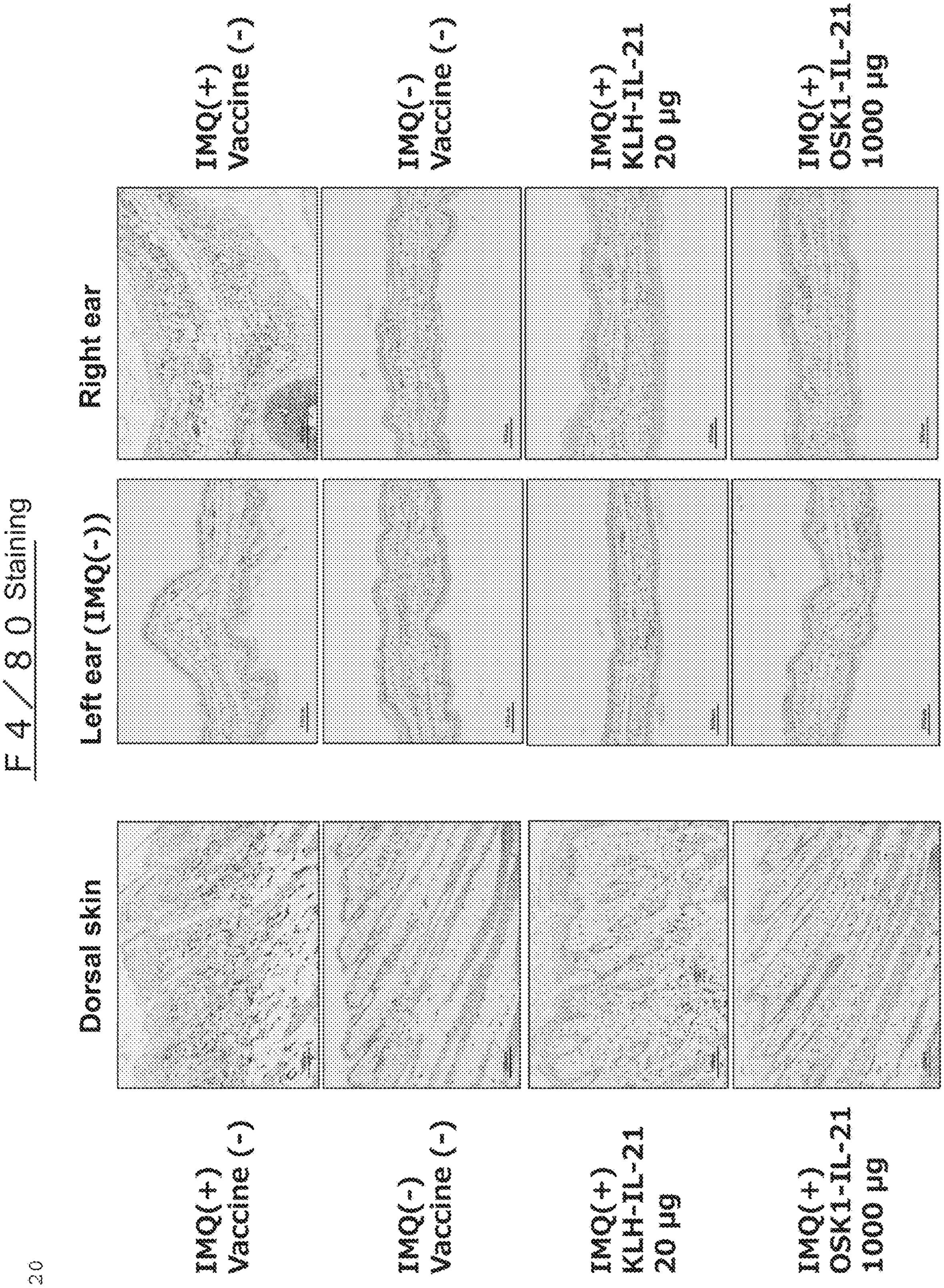
FIG. 20 shows the results of F4/80 staining of the skin of model mice of imiquimod-induced psoriasiform dermatitis on Day 12 after the start of psoriasis induction preceded by vaccination with the OSK-1-IL-17A conjugate or the KLH-IL-17A conjugate.
Figure 21:
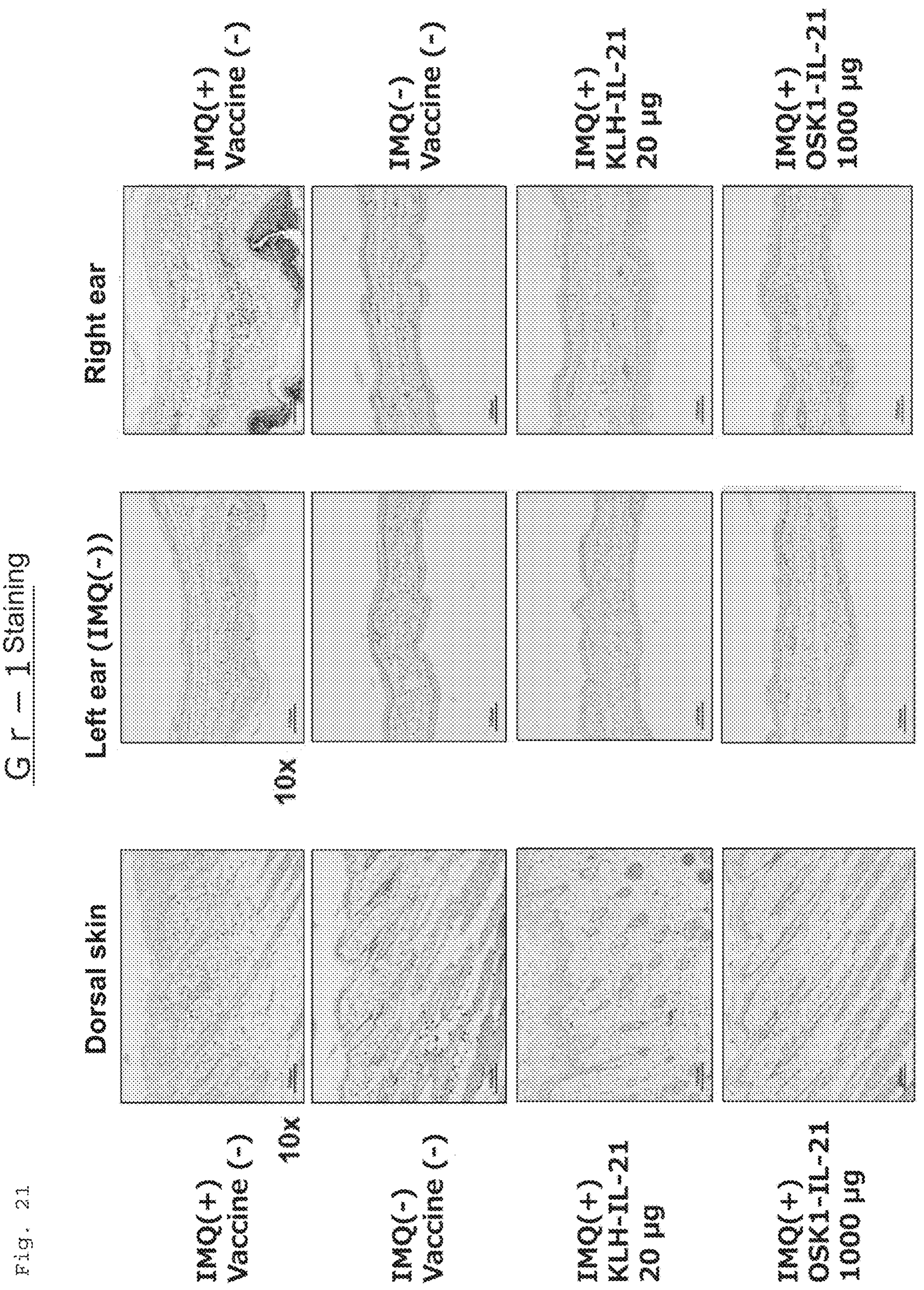
FIG. 21 shows the results of Gr-1 staining of the skin of model mice of imiquimod-induced psoriasiform dermatitis on Day 12 after the start of psoriasis induction preceded by vaccination with the OSK-1-IL-17A conjugate or the KLH-IL-17A conjugate.

The results of the involucrin staining are shown in FIG. 19, the results of the F4/80 staining are shown in FIG. 20, and the results of the Gr-1 staining are shown in FIG. 21. As shown in these results, the expression of involucrin, which was locally observed in the upper part of the stratum spinosum in the normal skin, was widely spread over the epidermis in the skin subjected to the application of imiquimod, representing a sign of enhanced keratinization. In the OSK-1-IL-17A conjugate administration group, this phenomenon was remarkably suppressed as compared with the KLH-IL-17A conjugate administration group. In the skin and the auricles subjected to the application of imiquimod, the number of macrophages, which are F4/80-positive cells, and the number of granulocytes, which are Gr-1-positive cells, were increased more remarkably. In the OSK-1-IL-17A conjugate administration group, infiltration of these immune cells was remarkably inhibited as compared with the KLH-IL-17A conjugate administration group.

(3) Blood IL-17 Concentration

Blood samples were collected before the start of psoriasis induction (Day 0) and on Day 12 after the start of psoriasis induction, and serum IL-17 concentration was measured using Mouse IL-17 A/F Heterodimer Quantikine ELISA Kit (R&D systems).

Figure 22:
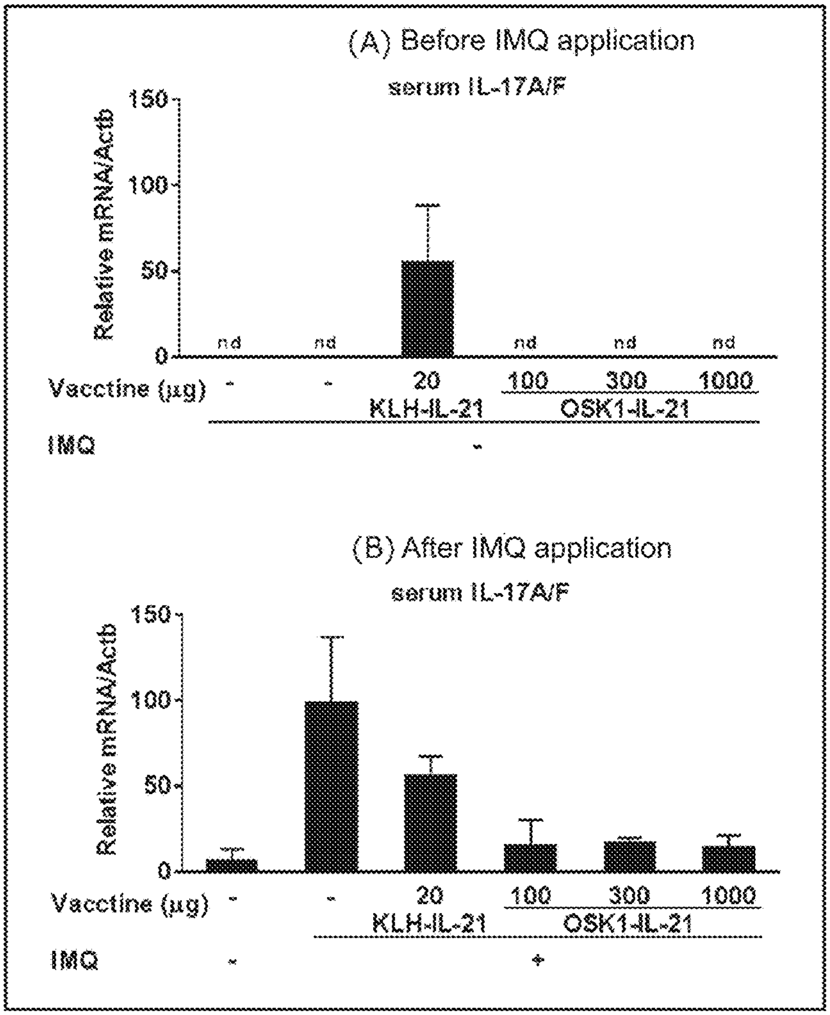
FIG. 22 shows the blood IL-17 concentration measured in model mice of imiquimod-induced psoriasiform dermatitis which had undergone vaccination with the OSK-1-IL-17A conjugate or the KLH-IL-17A conjugate prior to psoriasis induction.

The results are shown in FIG. 22. FIG. 22A shows the results of the mice before the application of imiquimod (Day 0), and FIG. 22B shows the results of the mice subjected to daily application of imiquimod (Day 12). As shown in FIG. 22B, in the OSK-1-IL-17A conjugate administration groups, the blood IL-17A/F concentrations were lower than that of the KLH-IL-17A conjugate administration group. In addition, as shown in FIG. 22A, only in the KLH-IL-17A conjugate administration group, the blood IL-17A/F concentration was elevated before the application of imiquimod.

(4) Expression of Inflammation-Related Factors in Psoriasis Lesions

On Day 12 after the start of psoriasis induction, the skin lesions of psoriasis were dissected, and RNA was extracted from the skin tissue using RNeasy Fibrous Tissue Mini Kit. The messenger RNA levels of the inflammation-related factors IL-17A, IL-17F, IL-22 and IL-23 were measured by real-time PCR using the primers and probe of TaqMan Gene Expression Assays.

As a result, the messenger RNA levels of the indicated factors were higher in the mice not subjected to administration of the OSK-1-IL-17A conjugate, but in the OSK-1-IL-17A conjugate administration groups, the expression of the messenger RNAs of the indicated factors was suppressed.

In Examples 9 and 10 shown above, model mice of imiquimod-induced psoriasiform dermatitis were used for the assessment of the medical efficacy of the OSK-1-IL-17A conjugate, but model mice of IL-23-induced psoriasiform dermatitis were also used for the same purpose. The specific procedure is described in, for example, W. Jiang et al. ("A Toll-Like Receptor 7, 8, and 9 Antagonist Inhibits Th1 and Th17 Responses and Inflammasome Activation in a Model of IL-23-Induced Psoriasis" W. Jiang, et al., 1784 Journal of Investigative Dermatology (2013), Volume 133) and is as follows. Six to eight-week-old C57BL/6 mice are prepared, and 0.5 mg of mouse IL-23 is dissolved in 20 mL of PBS. An aliquot of the mouse IL-23 solution is intracutaneously injected to the left ear of each mouse, for example, on Day 0, Day 2, Day 4, Day 6, Day 10, Day 12 and Day 14 to induce dermatitis. The mice with induced dermatitis are randomly assigned to groups, and the test sample or a control sample (for example, PBS) is administered to the corresponding group of mice. The test sample or the control sample is subcutaneously administered, for example, on Day 3, Day 6, Day 9, Day 12 and Day 15. The thickness of the auricle is measured with a digital caliper, for example, on Day 18. In addition, the auricle is dissected and histopathologically analyzed.

Example 11: Examination of Antibody Production Induced by OSK-1-IgE Conjugate

An OSK-1-IgE conjugate composed of the OSK-1 peptide (SEQ ID NO: 1) and a mouse IgE epitope peptide (SEQ ID NO: 23) via an ε-Acp linker was produced and intracutaneously administered to Balb/c mice at a dose of 100 or 250 μg per animal 3 times at 2-week intervals. Every 2 weeks after the first administration, blood samples were collected, and the antibody titer against the epitope peptide was measured by ELISA.

The antibody titers measured 8 weeks after the first administration are shown in Table 5. The antibody titer is expressed as a half maximum value.

TABLE 5

| IgE vaccine Half Maximum | | |
|---|---|---|
| | Half Maximum(8 W) | |
| ID | 100 μg | 250 μg |
| OSK1-IgE-23 | 4093. 3 | 10487. 0 |

Example 12: Examination of Antibody Production Induced by OSK-1-PCSK9 Conjugates Three types of OSK-1-PCSK9 conjugates composed of the OSK-1 peptide (SEQ ID NO: 1) conjugated to a mouse PCSK9 epitope peptide (SEQ ID NO: 25, 26 or 27) via an ε-Acp linker were produced and intracutaneously administered to Balb/c mice at a dose of 100 or 250 μg per animal 3 times at 2-week intervals. Every 2 weeks after the first administration, blood samples were collected, and the antibody titer against each epitope peptide was measured by ELISA.

The antibody titers measured 8 weeks after the first administration are shown in Table 6. The antibody titer is expressed as a half maximum value.

TABLE 6

| PCSK9 vaccine Half Maximum | | |
|---|---|---|
| | Half Maximum(8 W) | |
| ID | 100 μg | 250 μg |
| OSK1-PCSK9-25 | 21.4 | 434.2 |
| OSK1-PCSK9-26 | 2440.3 | NT |
| OSK1-PCSK9-27 | 1596.0 | 4632.1 |

NT: Not Tested

Example 13: Assessment of OSK-1-PCSK9 Conjugate by Blood PCSK9 Concentration Measurement The serum PCSK9 concentration was measured using the blood samples collected from the mice to which OSK1-

PCSK9-27 had been administered 3 times at a dose of 250 μg (the OSK-1-PCSK9 conjugate administration group) in Example 12. The blood samples were collected before the first administration and at 2, 4 and 6 weeks after the first administration. Separately, an OSK-1 administration group was prepared as a control, the administration of OSK-1 and the collection of blood samples were performed on the same schedule as employed in the OSK-1-PCSK9 conjugate administration group, and the serum PCSK9 concentration was measured. For the measurement of the serum PCSK9 concentration, Mouse Proprotein Convertase 9/PCSK9 Quantikine ELISA Kit (R&D systems) was used. It has been previously reported that the administration of a PCSK9 antibody induces the elevation of blood PCSK9 concentration. This phenomenon is considered to result from the stabilization of the PCSK9 protein by the antibody, which slows the elimination of the PCSK9 protein from the body. Based on this consideration, the elevation of the blood PCSK9 level by vaccination can be regarded as an evidence for the fact that the antibody produced by vaccination acts on its target protein (Peptide-Based Anti-PCSK9 Vaccines—An Approach for Long-Term LDLc Management, PLoS One. 2014; 9(12), An Anti-PCSK9 Antibody Reduces LDL-Cholesterol On Top Of A Statin And Suppresses Hepatocyte SREBP-Regulated Genes; Int. J. Biol. Sci. 2012, 8(3): 310-327).

Figure 23:
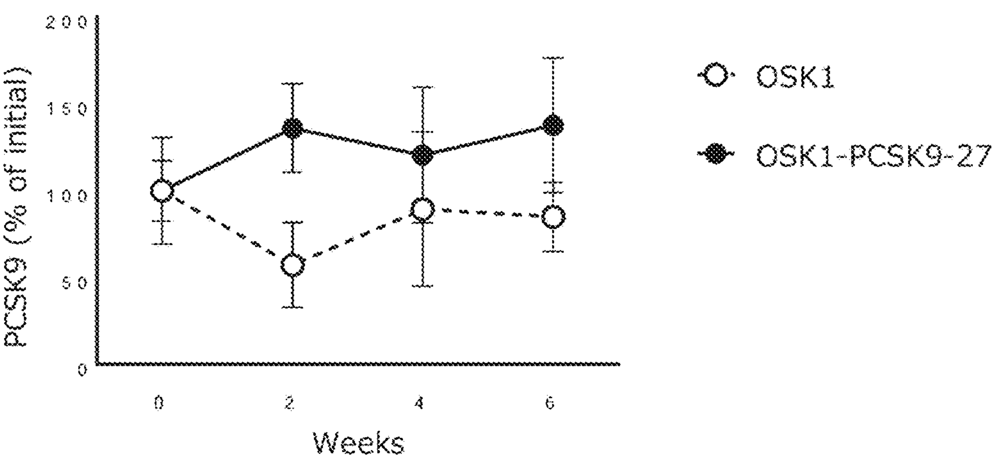
FIG. 23 shows the results of the assessment of the medical efficacy of an OSK-1-PCSK9 conjugate based on the blood PCSK9 concentration.

The results are shown in FIG. 23. In the OSK-1-PCSK9 conjugate administration group, the blood PCSK9 levels at 2 to 6 weeks after the first administration were elevated from the level before the first administration.

Reference Example 3: Effect of KLH-PCSK9 Conjugate on Blood Lipid Levels

For this test, a KLH-PCSK9 conjugate composed of a mouse PCSK9 epitope peptide (SEQ ID NO: 26) conjugated to KLH was used. Seven-week old ApoE deficient mice were purchased from Charles River Japan. The mice were assigned to a low-dose KLH-PCSK9 conjugate group (5 μg (PCSK9 peptide)/mouse), a high-dose KLH-PCSK9 conjugate group (50 μg (PCSK9 peptide)/mouse), a KLH administration group and a physiological saline administration group as a control. The amount of KLH administered to the mice of the KLH administration group was equal to the amount of KLH contained in the conjugate administered to the mice of the conjugate administration groups. The KLH-PCSK9 conjugate or KLH alone was mixed with an equal volume of Freund's adjuvant (Wako Pure Chemical Industries, Ltd.) before administration and the mixture was subcutaneously administered. Complete Freund's adjuvant was used at the first administration, and incomplete Freund's adjuvant was used at the second administration and later. The conjugates were administered 3 times in total (Day 0, Day 14 and Day 28). At 24 weeks after the final administration, blood samples were collected, and the lipid levels were measured. As a result, in the KLH-PCSK9 conjugate administration groups, the levels of CM (chylomicron) and VLDL were reduced to nearly half, and the level of TG (triglyceride) was reduced to nearly ⅔.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A vaccine comprising a complex of a peptide consisting of the amino acid sequence of SEQ ID NO: 1 and an epitope of a disease-causing biological protein, wherein the biological protein is IL-17A, and the epitope of IL-17A is a peptide consisting of the amino acid sequence of any of SEQ ID NOs: 10, 11, and 29 to 36.

2. The vaccine according to claim 1, wherein the epitope of the biological protein is conjugated to the peptide consisting of the amino acid sequence of SEQ ID NO: 1 via ε-aminocaproic acid.

3. The vaccine according to claim 1, wherein the amino acid at the N-terminus of the complex is acetylated.

4. The vaccine according to claim 1, wherein the amino acid at the C-terminus of the complex is amidated.

5. An immunogenic composition comprising a complex of a peptide consisting of the amino acid sequence of SEQ ID NO: 1 and an epitope of a disease-causing biological protein, wherein the biological protein is IL-17A, and the epitope of IL-17A is a peptide consisting of the amino acid sequence of any of SEQ ID NOs: 10, 11, and 29 to 36.

6. A complex for use in treatment of a disease caused by a biological protein, the complex of a peptide consisting of the amino acid sequence of SEQ ID NO: 1 and an epitope of the biological protein, wherein the biological protein IL-17A, and the epitope of IL-17A is a peptide consisting of the amino acid sequence of any of SEQ ID NOs: 10, 11, and 29 to 36.

7. A complex consisting of (a) the amino acid sequence of SEQ ID NO: 1, and (b) the amino acid sequence of SEQ ID NO: 10, wherein (a) is conjugated to (b) via ε-aminocaproic acid, wherein the amino acid at the N-terminus of the complex is acetylated, and wherein the amino acid at the C-terminus of the complex is amidated.

8. A complex consisting of (a) the amino acid sequence of SEQ ID NO: 1, and (b) the amino acid sequence of SEQ ID NO: 31, wherein (a) is conjugated to (b) via ε-aminocaproic acid, wherein the amino acid at the N-terminus of the complex is acetylated, and wherein the amino acid at the C-terminus of the complex is amidated.

9. A complex consisting of (a) the amino acid sequence of SEQ ID NO: 1, and (b) the amino acid sequence of SEQ ID NO: 32, wherein (a) is conjugated to (b) via ε-aminocaproic acid, wherein the amino acid at the N-terminus of the complex is acetylated, and wherein the amino acid at the C-terminus of the complex is amidated.

10. A complex consisting of (a) the amino acid sequence of SEQ ID NO: 1, and (b) the amino acid sequence of SEQ ID NO: 35, wherein (a) is conjugated to (b) via ε-aminocaproic acid, wherein the amino acid at the N-terminus of the complex is acetylated, and wherein the amino acid at the C-terminus of the complex is amidated.

* * * * *